(12) United States Patent
Turner et al.

(10) Patent No.: US 8,455,648 B2
(45) Date of Patent: Jun. 4, 2013

(54) 1-(7-(HEXAHYDROPYRROLO [3,4-C] PYRROL-2 (1H)-YL) QUINOLIN-4-YL) -3-(PYRAZIN-2-YL) UREA DERIVATIVES AND RELATED COMPOUNDS AS GLYCOGEN SYNTHASE KINASE 3 (GSK-3)

(75) Inventors: Sean Colm Turner, Mannheim (DE); Margaretha Henrica Maria Bakker, Ludwigshafen (DE); Wilfried Hornberger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 227 days.

(21) Appl. No.: 12/988,833

(22) PCT Filed: Apr. 24, 2009

(86) PCT No.: PCT/EP2009/054987
§ 371 (c)(1),
(2), (4) Date: Dec. 8, 2010

(87) PCT Pub. No.: WO2009/130317
PCT Pub. Date: Oct. 29, 2009

(65) Prior Publication Data
US 2011/0105528 A1    May 5, 2011

(30) Foreign Application Priority Data
Apr. 24, 2008 (EP) .................................... 08155133

(51) Int. Cl.
*C07D 215/38*    (2006.01)

(52) U.S. Cl.
USPC .............................. 546/167; 546/162; 546/159

(58) Field of Classification Search
USPC .......................................... 546/159, 162, 167
See application file for complete search history.

(56) References Cited

U.S. PATENT DOCUMENTS
2005/0209297 A1 * 9/2005 Sanner et al. ................ 514/406

FOREIGN PATENT DOCUMENTS

| WO | 00/47577 A1 | 8/2000 |
|---|---|---|
| WO | 03/049739 A1 | 6/2003 |
| WO | 2004/055009 A1 | 7/2004 |
| WO | 2007/017145 * | 2/2007 |
| WO | 2007/017145 A2 | 2/2007 |

OTHER PUBLICATIONS

Barth, B., et al., "Pyridazino[3,4-b][1,5] benzoxazepin-5(6H)-ones: synthesis and biological evaluation," Antiviral Chemistry & Chemotherapy (1996), vol. 7, No. 6, pp. 300-312.

Heinisch, G., et al., "Synthesis of pyridazino[3,4-b][1,5] benzodiazepin-5-ones and their biological evaluation as non-nucleoside HIV reverse transcriptase inhibitors," Arch. Pharm. Pharm. Med. Chem. 1997, 330, pp. 29-34.

Heinisch, G., et al., "Pyridazines, 81.1 A novel 1,2-diazone containing tricyclic system: synthesis of pyridazino[3,4-b] [1,5]-benzodiazepin-5-ones as potential HIV-1 reverse transcriptase inhibitors," Heterocycles, vol. 45, No. 4, 1997, pp. 673-682.

Heinisch, G., et al., "Synthesis of substituted tri- and tetracyclic compounds bearing a pyridzine core and their biological evaluation as antimycobacterial agents," Arch. Pharm. Pharm. Med. Chem. 2000, 333, pp. 231-240.

Porter, R., et al., "1,3-Biarylureas as selective non-peptide antagonists of the orexin-1 receptor," Bioorganic and Medicinal Chemistry Letters, vol. 11, No. 14, 2001, pp. 1907-1910.

Ott, I., et al., "Substituted pyridazino[3,4-b][1,5] benzoxazepin-5(6H) ones as multidrug-resistance modulating agents," J. Med. Chem. 2004, 47, pp. 4627-4630.

International Search Report from International Application Publication No. WO 2009/130317 A1.

Written Opinion from International Application Publication No. WO 2009/130317 A1.

* cited by examiner

*Primary Examiner* — D M Seaman
(74) *Attorney, Agent, or Firm* — Lisa V. Mueller; Michael Best & Friedrich LLP

(57) ABSTRACT

The present invention relates to novel heterocyclic compounds which are useful for inhibiting glycogen synthase kinase 3 (GSK-3), methods of making the compounds, compositions containing the compounds, and methods of treatment using the compounds.

19 Claims, No Drawings

1-(7-(HEXAHYDROPYRROLO [3,4-C] PYRROL-2 (1H)-YL) QUINOLIN-4-YL) -3- (PYRAZIN-2-YL) UREA DERIVATIVES AND RELATED COMPOUNDS AS GLYCOGEN SYNTHASE KINASE 3 (GSK-3)

CROSS REFERENCE TO RELATED APPLICATIONS

This application is the U.S. national stage entry of International Patent Application No. PCT/EP2009/054987, filed on Apr. 24, 2009, which claims the priority to European Patent Application No, EP08155133.5, filed on Apr. 24, 2008, the contents of which are hereby Incorporated by reference.

TECHNICAL FIELD

The present invention relates to novel heterocyclic compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β, with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy, argyrophilic grain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma.

GSK-3β may further have utility in the treatment of inflammatory diseases, such as rheumatoid arthritis and osteoarthritis.

GSK-3β may also have utility in the treatment of other diseases such as: Non-insulin dependent diabetes and obesity; osteoporosis; manic depressive illness; schizophrenia; alopecia; cancers such as breast cancer, non-small cell lung carcinoma, thyroid cancer, T or B-cell leukemia and several virus-induced tumors.

A review on GSK-3, its functions, its therapeutic potential and its possible inhibitors is given in "Glycogen Synthase Kinase 3 (GSK-3) and its inhibitors: Drug Discovery and Developments" by A. Martinez et al. (editors), John Wiley and Sons, 2006.

B. Barth et al. (Antiviral Chemistry & Chemotherapy 7 (6), 1996, 300-312) describe 6-alkyl substituted pyridazino[3,4-b][1,5]benzoxazepin-5-ones which are useful as inhibitors of HIV-1 reverse transcriptase. They also describe several pyridazino[3,4-b][1,5]benzoxazepin-5(6H)-ones being unsubstituted at the nitrogen as intermediates, namely pyridazino[3,4-b][1,5]benzoxazepin-5(6H)-one, 3-chloropyridazinobenzo[3,4-b][1,5]benzoxazepin-5(6H)-one, 3-chloro-8-trifluoromethylpyridazino[3,4-b][1,5]benzoxazepin-5(6H)-one, 3-chloro-8-methylpyridazino[3,4-b][1,5]benzoxazepin-5(6H)-one, 3-chloro-9-methylpyridazino[3,4-b][1,5]benzoxazepin-5(6H)-one, 3-chloro-8-methoxypyridazino[3,4-b][1,5]benzoxazepin-5(6H)-one and 3-chloro-8,10-dim ethylpyridazinobenzo[3,4-b][1,5]benzoxazepin-5(6H)-one.

G. Heinisch et al. (Arch. Pharm. Pharm. Med. Chem. 2000, 333, 231-240) describe pyridazinobenzo[3,4-b][1,5]benzoxazepin-5(6H)-ones being unsubstituted at the nitrogen as intermediates in the synthesis of the corresponding N-alkyl derivatives, namely 3-chloropyridazinobenzo[3,4-b][1,5]benzoxazepin-5(6H)-one, 3,8-dichloropyridazino[3,4-b][1,5]benzoxazepin-5(6H)-one, 3-chloro-8-methylpyridazino[3,4-b][1,5]benzoxazepin-5(6H)-one and 3-chloro-9-methylpyridazino[3,4-b][1,5]benzoxazepin-5(6H)-one.

I. Ott et al. (J. Med. Chem. 2004, 47, 4627-4630) describe 6-alkyl substituted pyridazinobenzo[3,4-b][1,5]benzoxazepin-5-ones which are useful as Multidrug-Resistance Modulating agents in tumor therapy. They also describe several pyridazinobenzo[3,4-b][1,5]benzoxazepin-5(6H)-ones being unsubstituted at the nitrogen as intermediates, e.g. 3-chloro-9-trifluoromethylpyridazino[3,4-b][1,5]benzoxazepin-5(6H)-one.

G. Heinisch et al. (Arch. Pharm. Pharm. Med. Chem. 1997, 330, S. 29-34 and Heterocycles 1997, 45, 673-682) describe inter alia 3-chloro-8-nitro-11-propylpyridazino[3,4-b][1,5]benzodiazipin-5-one.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative and/or inflammatory diseases. More specifically, the goal is to provide novel compounds useful as an active ingredient of a composition that enables prevention and/or treatment of neurodegenerative diseases such as Alzheimer's disease.

It was surprisingly found that the problem is solved by providing a heterocyclic compound of the general formula I

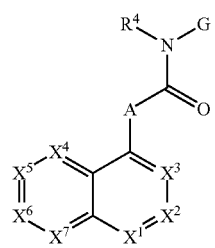

(I)

the stereoisomers, prodrugs, tautomers and/or physiologically tolerated acid addition salts thereof, wherein A is selected from the group consisting of $CR^{A1}R^{A2}$ and $NR^B$; where
  $R^{A1}$ and $R^{A2}$ are independently of each other selected from the group consisting of hydrogen, $C_1$-$C_2$-alkyl, $C_1$-$C_2$-haloalkyl, $NH_2$ and OH; and
  $R^B$ is selected from H, $C_1$-$C_4$-alkyl and $C_1$-$C_4$-haloalkyl;
$X^1$, $X^2$ and $X^3$ are independently of each other selected from the group consisting of $CR^2$ and N;
$X^4$, $X^5$, $X^6$ and $X^7$ are independently of each other selected from the group consisting of $CR^1$, $CR^3$ and N;
  with the proviso that at least one of $X^1$, $X^2$, $X^3$, $X^4$, $X^5$, $X^6$ and $X^7$ is N and that no more than two of $X^4$, $X^5$, $X^6$ and $X^7$ are $CR^1$;
G is a 5- or 6-membered heteroaromatic ring containing one nitrogen atom and optionally 1, 2 or 3 further nitrogen atoms as ring members, where the heteroaromatic ring is bonded via a carbon atom in α-position to the nitrogen ring atom to the group $NR^4$ and where the heteroaromatic ring optionally carries 1, 2, 3 or 4 substituents $R^5$ or 1, 2 or 3 substituents $R^5$ and 1 substituent $R^1$;
  with the proviso that or G carries one substituent $R^1$ if none of $X^4$, $X^5$, $X^6$ and $X^7$ is $CR^1$;
each $R^1$ is independently a 6-, 7-, 8-, 9-, 10-, 11-, 12-, 13- or 14-membered bicyclic or tricyclic saturated or unsaturated heterocyclic ring containing one nitrogen atom and optionally 1, 2 or 3 further heteroatoms selected from N, O and S as ring members and optionally carrying 1, 2 or 3 substituents $R^6$;
each $R^2$ is independently selected from the group consisting of hydrogen, OH, halogen, CN, $C_1$-$C_6$-alkyl, $C_1$-$C_6$-haloalkyl and $NR^aR^b$;
  or two radicals $R^2$ bonded at the carbon atoms of groups $X^2$ and $X^3$, together with the carbon atoms to which they are bonded, form a 5- or 6-membered saturated or unsaturated ring which may contain 1 or 2 heteroatoms as ring members selected from the group consisting of N, O and S and which optionally carries 1, 2 or 3 substituents $R^7$;
each $R^3$ is independently selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^8$ and wherein Ar may also be bondd via a $CH_2$ group;
$R^4$ is selected from the group consisting of hydrogen, $C_1$-$C_4$-alkyl and $C_1$-$C_4$-haloalkyl;
$R^5$, $R^6$ and $R^7$, independently of each other and independently of each occurrence, have one of the meanings given for $R^3$;
each $R^8$ is independently selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, a phenyl group and an aromatic 5- or 6-membered C-bound heteroaromatic radical comprising one nitrogen atom and optionally 1, 2 or 3 further heteroatoms independently selected from O, S and N as ring members, wherein phenyl and the heteroaromatic radical are, independently of each other, unsubstituted or substituted by 1, 2, 3 or 4 radicals selected from halogen, cyano, $C_1$-$C_4$-alkyl, $C_1$-$C_4$-haloalkyl, $C_1$-$C_4$-alkoxy and $C_1$-$C_4$-haloalkoxy; and
$R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-haloalkylcarbonyl;
or $R^a$ and $R^b$ form, together with the nitrogen atom to which they are bonded, a 3-, 4-, 5-, 6- or 7-membered saturated or unsaturated aromatic or non-aromatic N-heterocyclic ring, which may contain 1 further heteroatom or heteroatom containing group selected from the group consisting of O, S, SO, $SO_2$ and N as a ring member.

Thus, the present invention relates to compounds of the formula I as defined herein and in the claims, to the stereoisomers, tautomers, prodrugs and/or physiologically tolerated acid addition salts thereof.

According to a further aspect, the present invention relates to a pharmaceutical composition comprising at least one compound of the formula I as defined herein, a stereoisomer, a tautomer, a prodrug and/or a physiologically tolerated acid addition salt thereof, optionally together with at least one physiologically acceptable carrier and/or auxiliary substance.

According to a further aspect, the present invention relates to the use of at least one compound of the formula I as defined herein, the stereoisomers, tautomers, prodrugs and/or physiologically tolerated acid addition salts thereof, for the preparation of a pharmaceutical composition for the treatment of a medical disorder susceptible to treatment with a compound that modulates glycogen synthase kinase 3β activity.

According to a further aspect, the present invention relates to a method for treating a medical disorder susceptible to treatment with a compound that modulates glycogen synthase kinase 3β activity, said method comprising administering an effective amount of at least one compound of the formula I as defined herein, a stereoisomer, a tautomer, a prodrug and/or a physiologically tolerated acid addition salt thereof, to a subject in need thereof.

DETAILED DESCRIPTION OF THE INVENTION

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhäuser Verlag, Basel and Stuttgart, 1966.

In the terms of the present invention, "prodrugs" are compounds which are metabolized in vivo to give the compounds of the invention of formula I. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula I wherein an external nitrogen atom, for example a secondary nitrogen ring atom of the heterocyclic group $R^1$ or a nitrogen atom of a primary or secondary amino group being a substituent $R^2$, $R^3$, $R^5$, $R^6$, $R^7$ and/or $R^8$ (=at least one of $R^2$, $R^3$, $R^5$, $R^6$, $R^7$ and $R^8$ is $NR^aR^b$, wherein at least one of $R^a$ and $R^b$ is H), forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein R$^x$ and R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds I wherein said nitrogen atom carries a hydrogen atom instead.

The compounds of formula I may also be present in the form of the respective tautomers. This is for instance the case for compounds I wherein $R^2$ and/or $R^3$ are OH and these substituents are bonded to a carbon atom which is in α-position to a nitrogen ring atom. This results for example in following tautomeric formulae:

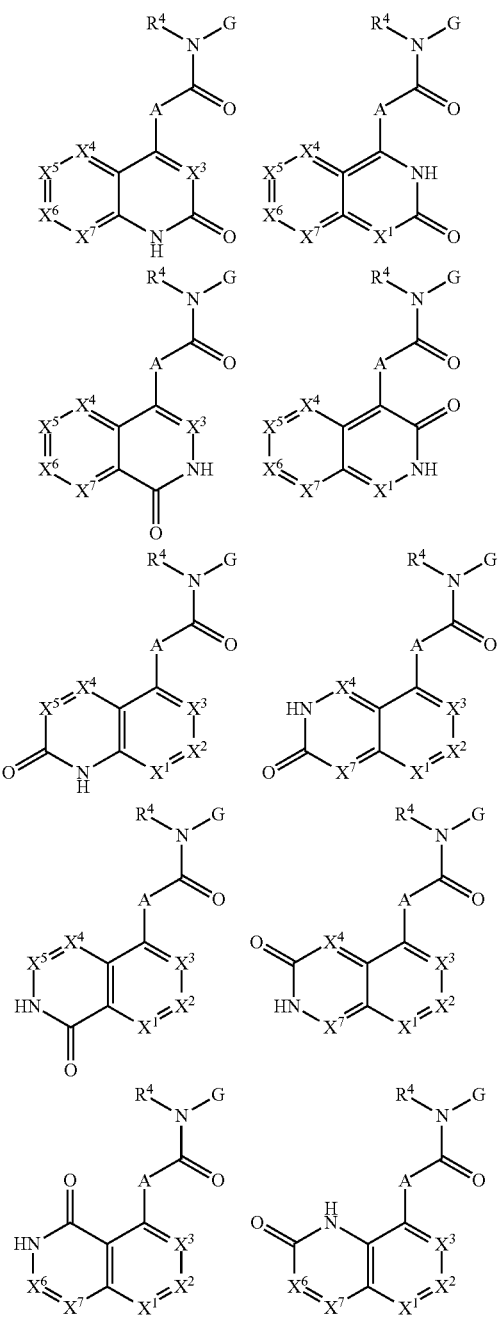

The organic moieties mentioned in the above definitions of the variables are—like the term halogen—collective terms for individual listings of the individual group members. The prefix $C_n$—$C_m$ indicates in each case the possible number of carbon atoms in the group.

The term halogen denotes in each case fluorine, bromine, chlorine or iodine, in particular fluorine, chlorine or bromine.

$C_1$-$C_2$-Alkyl is methyl or ethyl; $C_1$-$C_3$-alkyl is additionally n-propyl or isopropyl.

$C_1$-$C_4$-Alkyl is a straight-chain or branched alkyl group having from 1 to 4 carbon atoms. Examples are methyl, ethyl, n-propyl, isopropyl, n-butyl, 2-butyl(sec-butyl), isobutyl and tert-butyl.

$C_1$-$C_6$-Alkyl is a straight-chain or branched alkyl group having from 1 to 6 carbon atoms. Examples include the residues mentioned above for $C_1$-$C_4$-alkyl and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dim ethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_2$-Haloalkyl is an alkyl group having 1 or 2 carbon atoms (as mentioned above), where at least one of the hydrogen atoms, e.g. 1, 2, 3, 4 or 5 hydrogen atoms in these groups are replaced by halogen atoms as mentioned above, such as chloromethyl, dichloromethyl, trichloromethyl, fluoromethyl, difluoromethyl, trifluoromethyl, bromomethyl, chlorofluoromethyl, dichlorofluoromethyl, chlorodifluoromethyl, 1-chloroethyl, 1-bromoethyl, 1-fluoroethyl, 2-chloroethyl, 2-bromoethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

$C_1$-$C_4$-Haloalkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by halogen atoms as mentioned above. Examples are, apart those listed above for $C_1$-$C_2$-haloalkyl, 1-chloropropyl, 1-bromopropyl, 1-fluoropropyl, 2-chloropropyl, 2-bromopropyl, 2-fluoropropyl, 3-chloropropyl, 3-bromopropyl, 3-fluoropropyl, 1,1-dichloropropyl, 1,1-difluoropropyl, 2,2-dichloropropyl, 2,2-difluoropropyl, 2,3-dichloropropyl, 2,3-difluoropropyl, 1,3-dichloropropyl, 1,3-difluoropropyl, 3,3-dichloropropyl, 3,3-difluoropropyl, 1,1,2-trichloropropyl, 1,1,2-trifluoropropyl, 1,2,2-trichloropropyl, 1,2,2-trifluoropropyl, 1,2,3-trichloropropyl, 1,2,3-trifluoropropyl, 2,2,3-trichloropropyl, 2,2,3-trifluoropropyl, 3,3,3-trichloropropyl, 3,3,3-trifluoropropyl, 1,1,1-trifluoroprop-2-yl, 1-chlorobutyl, 1-bromobutyl, 1-fluorobutyl, 2-chlorobutyl, 2-bromobutyl, 2-fluorobutyl, 3-chlorobutyl, 3-bromobutyl, 3-fluorobutyl, 4-chlorobutyl, 4-bromobutyl, 4-fluorobutyl, and the like.

$C_1$-$C_6$-Haloalkyl is a straight-chain or branched alkyl group having 1 to 6 carbon atoms (as mentioned above), where at least one of the hydrogen atoms in these groups is replaced by halogen atoms as mentioned above. Examples are, apart those listed above for $C_1$-$C_4$-haloalkyl, chloropentyl, bromopentyl, fluoropentyl, chlorohexyl, bromohexyl, fluorohexyl, and the like.

$C_1$-$C_2$-Fluoroalkyl (=fluorinated $C_1$-$C_2$-alkyl) is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl.

$C_1$-$C_4$-Fluoroalkyl (=fluorinated $C_1$-$C_4$-alkyl) is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like.

$C_1$-$C_6$-Fluoroalkyl (=fluorinated $C_1$-$C_6$-alkyl) is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 65-fluorohexyl, (R)-6-fluorohexyl, (S)-6-fluorohexyl, and the like.

$C_1$-$C_4$-Alkoxy is a straight-chain or branched alkyl group having from 1 to 4 carbon atoms, which is bound to the remainder of the molecule via an oxygen atom. Examples include methoxy, ethoxy, n-propoxy, isopropoxy, n-butoxy, 2-butoxy, isobutoxy and tert-butoxy.

$C_1$-$C_6$-Alkoxy is a straight-chain or branched alkyl group having from 1 to 6 carbon atoms, which is bound to the remainder of the molecule via an oxygen atom. Examples include, apart those listed above for $C_1$-$C_4$-alkoxy, pentyloxy, 1-methylbutoxy, 2-methylbutoxy, 3-methylbutoxy, 2,2-dimethylpropoxy, 1-ethylpropoxy, hexyloxy, 1,1-dim ethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dim ethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy (which is also termed $C_1$-$C_6$-haloalkoxy), in particular fluorinated $C_1$-$C_6$-alkoxy (also termed $C_1$-$C_6$-fluoroalkoxy) is a straight-chain or branched alkoxy group having from 1 to 6, in particular 1 to 4 carbon atoms (=fluorinated $C_1$-$C_4$-alkoxy), wherein at least one, e.g. 1, 2, 3, 4 or all of the hydrogen atoms are replaced by a halogen atoms, in particular fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_4$-Alkylcarbonyl is a straight-chain or branched alkyl group having from 1 to 4 carbon atoms), which is bound to the remainder of the molecule via a carbonyl group (CO), such as in acetyl, propionyl, isopropylcarbonyl, butylcarbonyl, sec-butylcarbonyl, isobutylcarbonyl, and tert-butylcarbonyl.

$C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonyl, pentylcarbonyl, hexylcarbonyl and the constitutional isomers thereof.

$C_1$-$C_4$-Haloalkylcarbonyl is a straight-chain or branched haloalkyl group having from 1 to 4 carbon atoms as defined above, which is bound to the remainder of the molecule via a carbonyl group (CO)

$C_1$-$C_6$-Haloalkylcarbonyl is a straight-chain or branched haloalkyl group having from 1 to 6 carbon atoms as defined above, which is bound to the remainder of the molecule via a carbonyl group (CO)

$C_1$-$C_4$-Fluoroalkylcarbonyl is a straight-chain or branched fluoroalkyl group having from 1 to 4 carbon atoms as defined above, which is bound to the remainder of the molecule via a carbonyl group (CO)

$C_1$-$C_6$-fluoroalkylcarbonyl is a straight-chain or branched fluoroalkyl group having from 1 to 6 carbon atoms as defined above, which is bound to the remainder of the molecule via a carbonyl group (CO)

$C_1$-$C_6$-Alkoxycarbonyl is a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

$C_1$-$C_6$-Haloalkoxycarbonyl is a straight-chain or branched haloalkoxy group having from 1 to 6, especially 1 to 4 carbon atoms (=$C_1$-$C_4$-haloalkoxycarbonyl), in particular 1 to 3 carbon atoms (=$C_1$-$C_3$-haloalkoxycarbonyl) as defined above, which is bound to the remainder of the molecule via a carbonyl group (CO).

$C_1$-$C_6$-Fluoroalkoxycarbonyl is a straight-chain or branched fluorooalkoxy group having from 1 to 6, especially 1 to 4 carbon atoms (=$C_1$-$C_4$-fluoroalkoxycarbonyl), in particular 1 to 3 carbon atoms (=$C_1$-$C_3$-fluoroalkoxycarbonyl) as defined above, which is bound to the remainder of the molecule via a carbonyl group (CO).

$C_3$-$C_6$-Cycloalkyl is a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. If substituted, one alkyl radical is preferably located in the 1-position of the cycloalkyl radical, such as in 1-methylcyclopropyl or 1-methylcyclobutyl. Likewise, $C_3$-$C_4$-cycloalkyl is a cycloaliphatic radical having from 3 to 4 C atoms, such as cyclopropyl and cyclobutyl.

$C_3$-$C_7$-Cycloalkyl is a cycloaliphatic radical having from 3 to 7 C atoms, such as cyclopropyl, cyclobutyl, cyclopentyl, cyclohexyl and cycloheptyl. The cycloalkyl radical may be unsubstituted or may carry 1, 2, 3 or 4 $C_1$-$C_4$ alkyl radicals, preferably a methyl radical. If substituted, one alkyl radical is preferably located in the 1-position of the cycloalkyl radical, such as in 1-methylcyclopropyl or 1-methylcyclobutyl.

$C_3$-$C_6$-Halocycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a halogen atoms, preferably by fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_7$-Halocycloalkyl is a cycloaliphatic radical having from 3 to 7 C atoms, such as cyclopropyl, cyclobutyl, cyclopentyl, cyclohexyl and cycloheptyl, wherein at least one, e.g. 1, 2, 3, 4 or all of the hydrogen atoms are replaced by a halogen atoms, preferably by fluorine atoms. Examples include, apart those listed above for $C_3$-$C_6$-fluorocycloalkyl, 1-fluorocycloheptyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

$C_2$-$C_4$-Alkenyl is a singly unsaturated hydrocarbon radical having 2, 3 or 4 C-atoms, e.g. vinyl, allyl (2-propen-1-yl), 1-propen-1-yl, 2-propen-2-yl, methallyl (2-methylprop-2-en-1-yl) and the like.

$C_2$-$C_4$-Haloalkenyl is a singly unsaturated hydrocarbon radical having 2, 3 or 4 C-atoms, wherein at least one, e.g. 1, 2, 3, 4 or all of the hydrogen atoms are replaced by halogen atoms, preferably by fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

Examples for 5- or 6-membered heteroaromatic rings containing one nitrogen atom and optionally 1, 2 or 3 further nitrogen atoms as ring members, where the heteroaromatic ring is bonded via a carbon atom in α-position to the nitrogen atom, are pyrrol-2-yl, pyrazol-3-yl, pyrazol-5-yl, imidazol-2-yl, imidazol-4-yl, imidazol-5-yl, [1,2,3]-1H-triazol-4-yl, [1,2,3]-1H-triazol-5-yl, [1,2,3]-2H-triazol-4-yl, [1,2,3]-2H-triazol-5-yl, [1,2,4]-1H-triazol-3-yl, [1,2,4]-1H-triazol-5-yl, [1,2,4]-4H-triazol-3-yl, [1,2,3,4]-1H-tetrazol-5-yl, [1,2,3,4]-2H-tetrazol-5-yl, pyridin-2-yl, pyridazin-3-yl, pyrimidin-2-yl, pyrimidin-4-yl, pyrazin-2-yl and triazin-2-yl.

Examples for 5- or 6-membered N- or C-bound heteroaromatic radicals comprising one nitrogen atom and optionally 1, 2 or 3 further heteroatoms independently selected from O, S and N as ring members are pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-3-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for N-bound 3-, 4-, 5-, 6- or 7-membered saturated or unsaturated aromatic or non-aromatic N-heterocyclic rings, which may contain 1 further heteroatom or heteroatom-containing group selected from the group consisting of O, S, SO, SO$_2$ and N as a ring member, are aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-1-yl, [1,2,3]-triazolidin-1-yl, [1,2,3]-triazolidin-2-yl, [1,2,4]-triazolidin-1-yl, [1,2,4]-triazolidin-4-yl, piperidin-1-yl, piperazin-1-yl, morpholin-4-yl, thiomorpholin-1-yl, 1-oxothiomorpholin-1-yl, 1,1-dioxothiomorpholin-1-yl, azepan-1-yl, azirin-1-yl, azetin-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

6-, 7-, 8-, 9-, 10-, 11-, 12-, 13- or 14-membered bicyclic or tricyclic rings are preferably 6-, 7-, 8-, 9-, 10-, 11 or 12-membered bicyclic rings or are 8-, 9-, 10-, 11-, 12-, 13- or 14-membered tricyclic rings.

Examples for 6-, 7-, 8-, 9-, 10-, 11-, 12-, 13- or 14-membered bicyclic or tricyclic saturated or unsaturated heterocyclic ring containing one nitrogen atom and optionally 1, 2 or 3 further heteroatoms selected from N, O and S as ring members and optionally carrying 1, 2 or 3 substituents R$^6$ include the radicals of the following formulae:

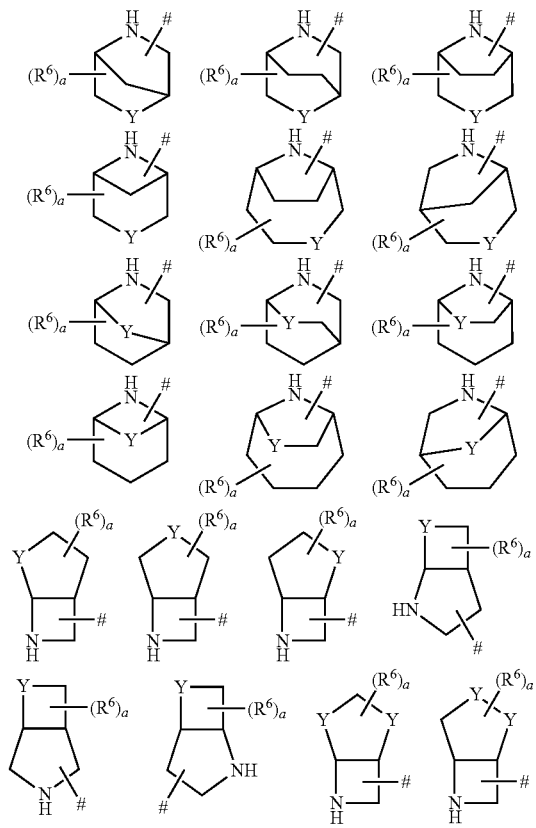

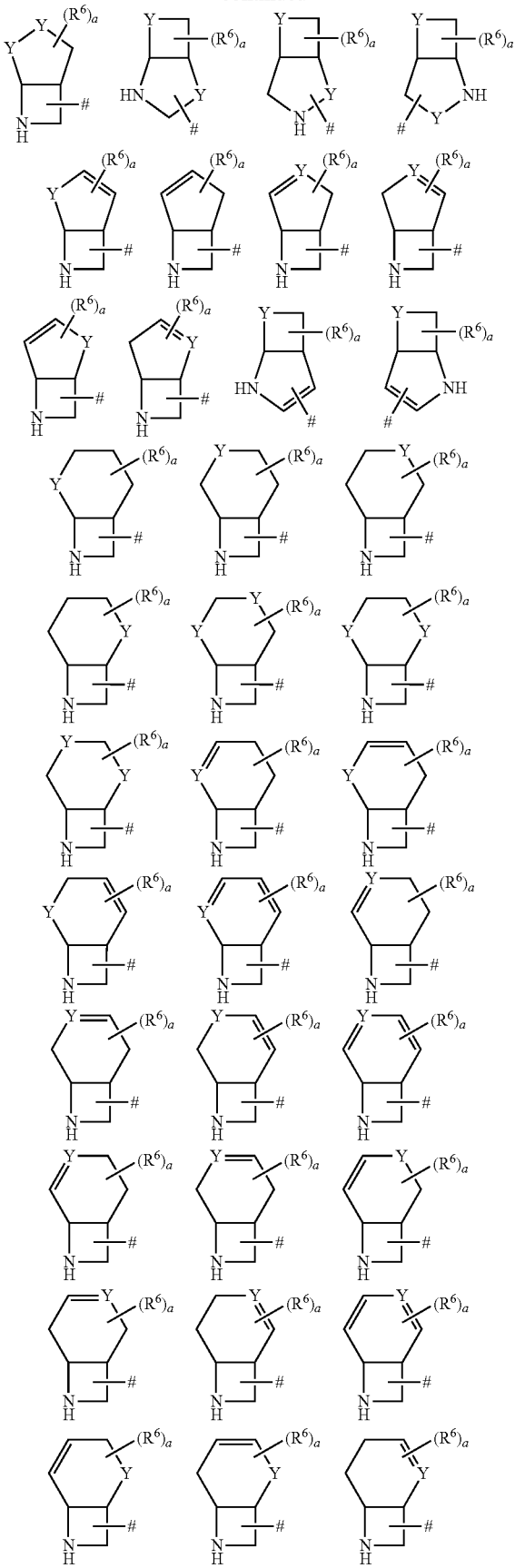

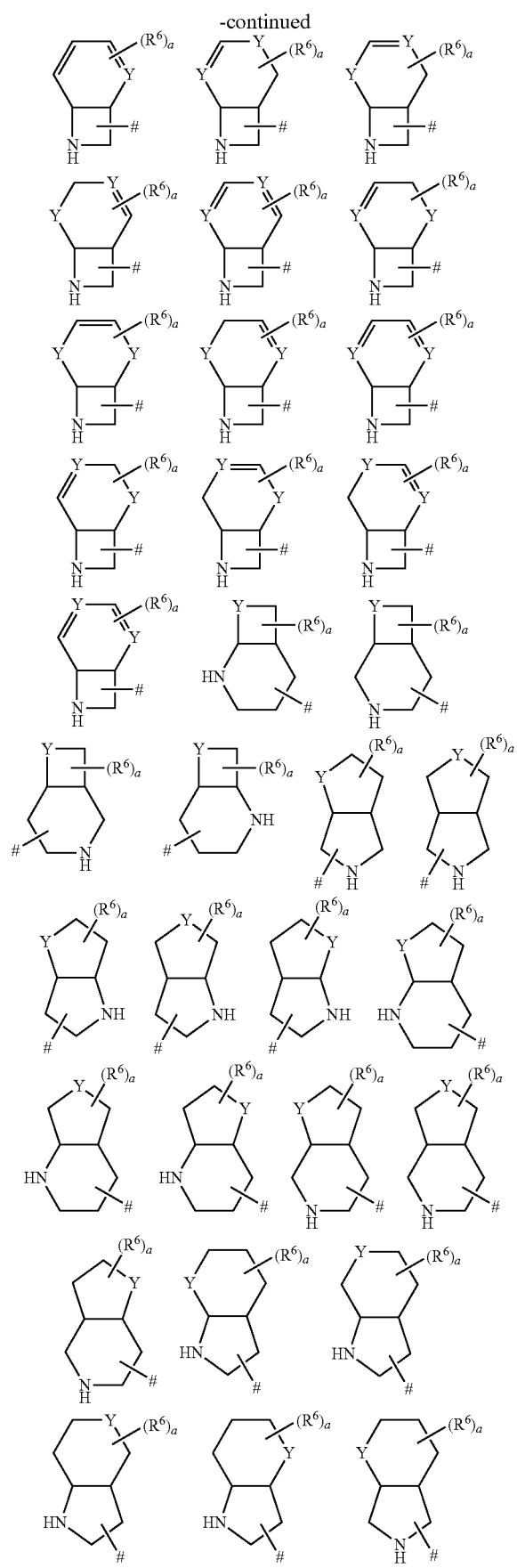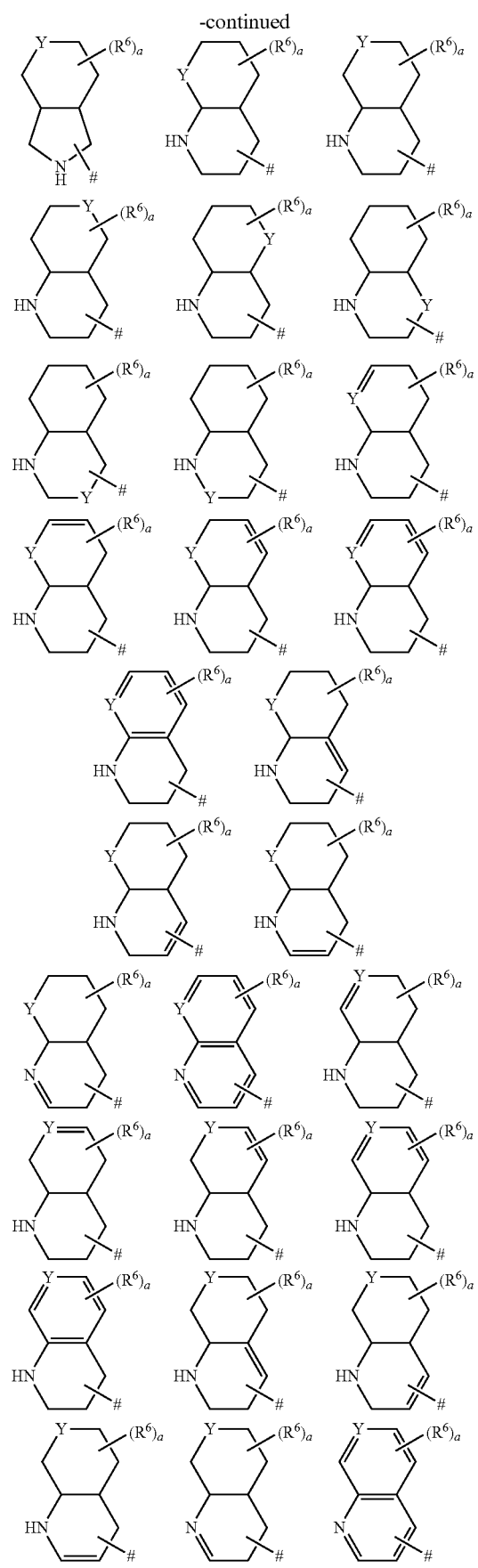

-continued
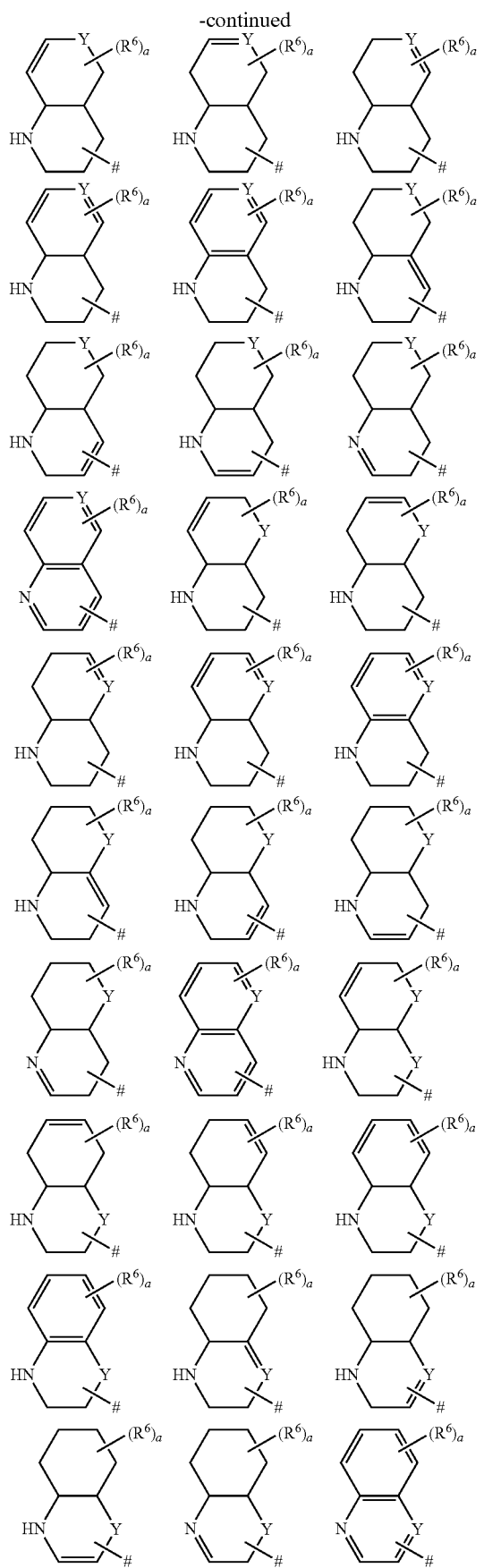
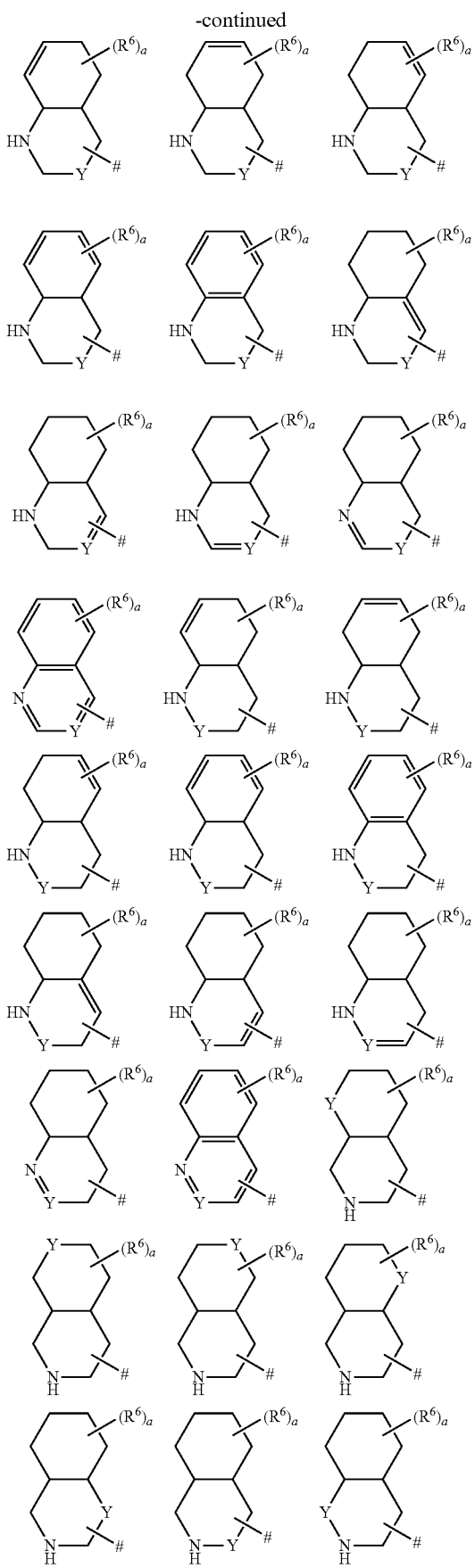

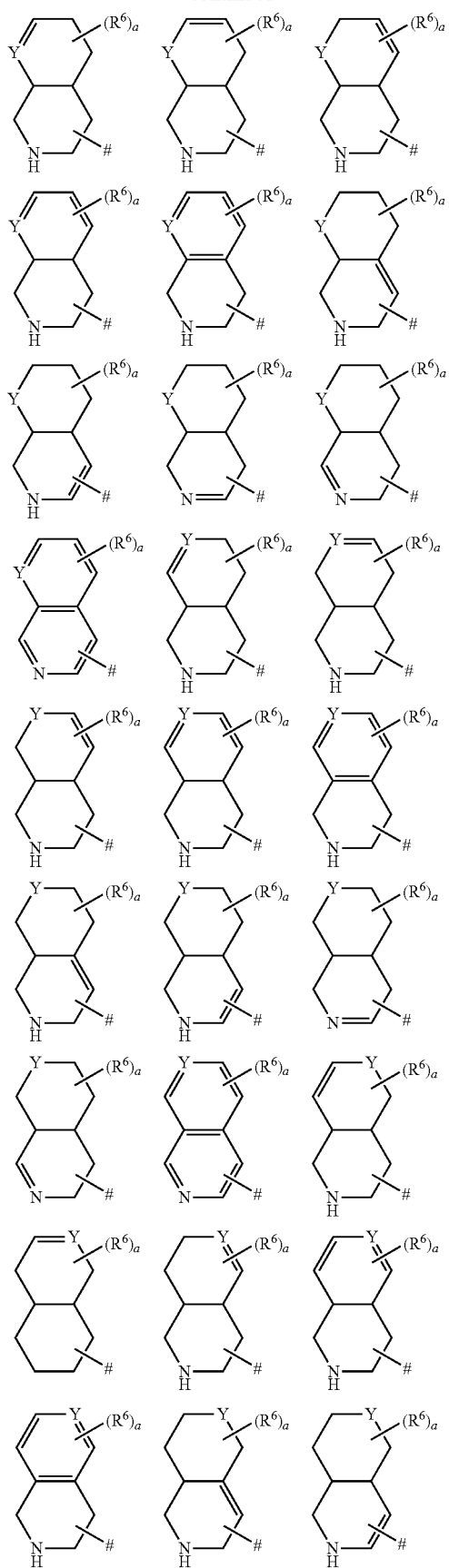
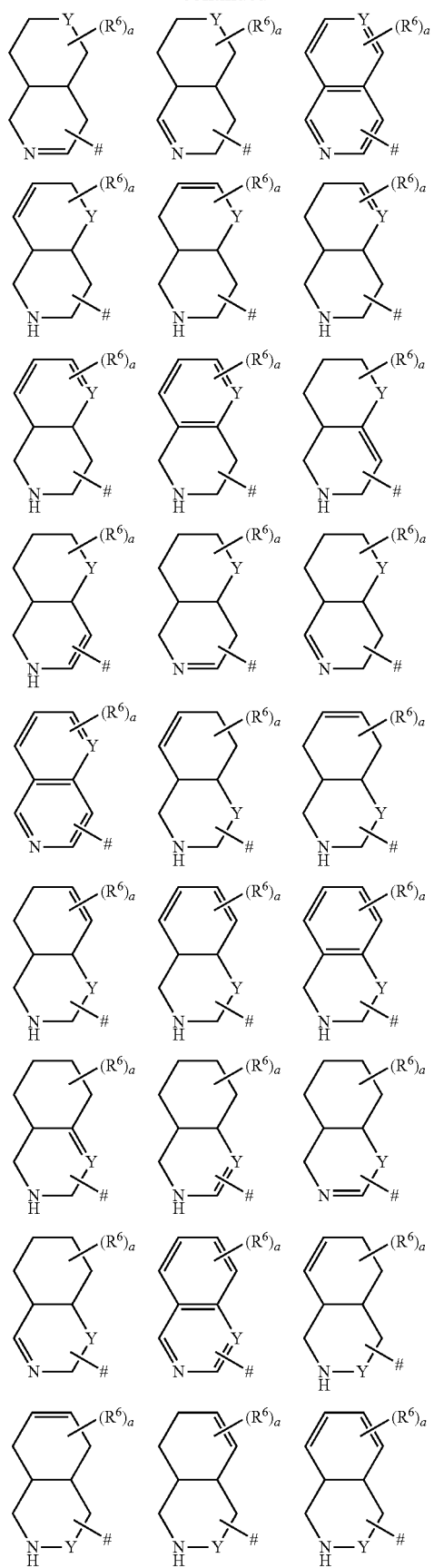

-continued

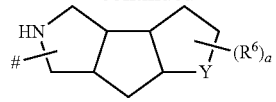

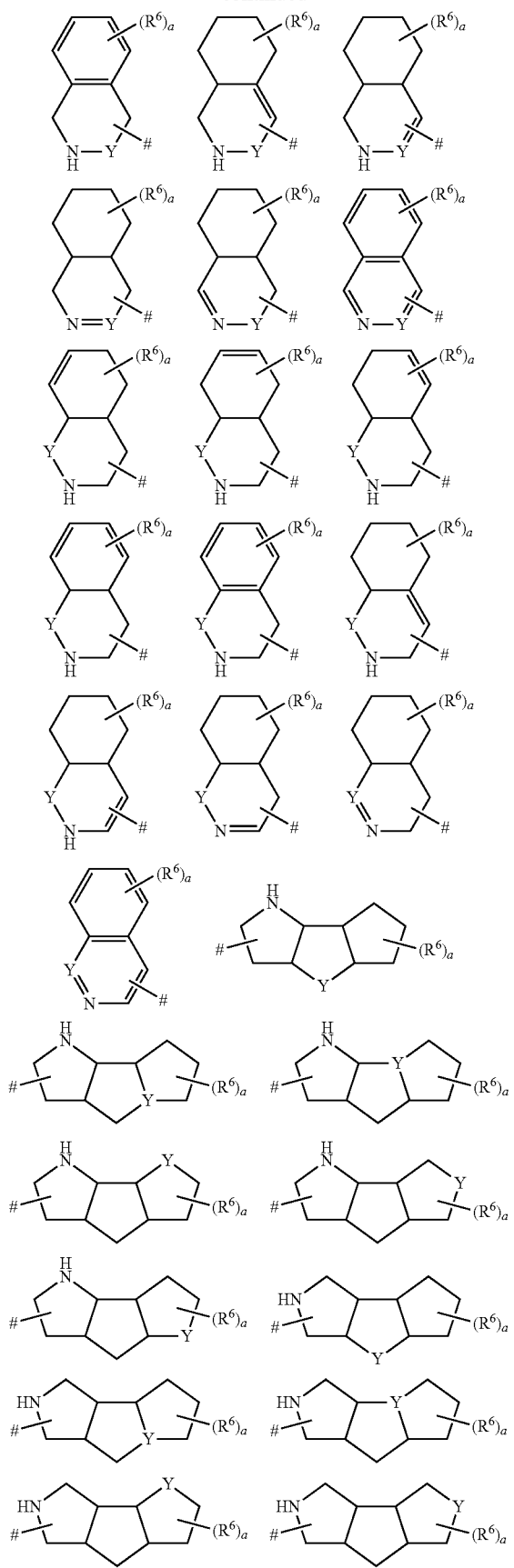

and the like and all stereoisomers thereof, where
Y is $CH_2$, CH (if Y is part of a double bond or is a bridge atom), NH, N (if Y is part of a double bond or is a bridge atom), O or S, preferably NH or O and more preferably NH, with the proviso that Y is not O or S if Y is part of a double bond or a bridge atom;
$R^6$ has one of the general meanings given above or one of the preferred meanings given below;
a is 0, 1, 2 or 3, preferably 0, 1 or 2 and more preferably 0 or 1; and
# is the attachment point to the remainder of the molecule.
$R^6$ and/or the attachment point can also be located on a nitrogen atom where they replace the hydrogen atom. $R^6$ and the attachment point can also be located on the same ring or be switched in the above formulae. However, they are preferably located on different rings and as shown above. Preferably, the attachment point is located on a nitrogen atom. $R^6$, if present, is preferably also located on a nitrogen atom.

The remarks made above and in the following with respect to preferred aspects of the invention, e.g. to preferred meanings of the variables $X^1$, $X^2$, $X^3$, $X^4$, $X^5$, $X^6$, $X^7$, $R^1$, $R^2$, $R^3$, $R^4$, $R^5$, $R^6$, $R^7$, $R^8$, $R^{61}$, $R^a$, $R^b$, $R^{A1}$m, $R^{A2}$, $R^B$, A, G of compound I, to preferred compounds I and to preferred embodiments of the method or the use according to the invention, apply in each case on their own or in particular to combinations thereof.

The compounds of the invention are characterized by having one or two substituents $R^1$ bonded to the condensed heteroaromatic system (to be more precise on the position of groups $X^4$, $X^5$, $X^6$ and/or $X^7$) and/or one substituent $R^1$ bonded to the heteroaromatic ring G.

In a preferred embodiment of the invention, one or two of groups $X^4$, $X^5$, $X^6$ and $X^7$ are $CR^1$. In this case, the heteroaromatic ring G preferably doesn't carry a substituent $R^1$. More preferably, only one of groups $X^4$, $X^5$, $X^6$ and $X^7$ is $CR^1$. In this case, too, the heteroaromatic ring G preferably doesn't carry a substituent $R^1$.

If one or two of groups $X^4$, $X^5$, $X^6$ and $X^7$ are $CR^1$, it is preferred that one or two of the groups $X^5$, $X^6$ and $X^7$ are $CR^1$, $X^4$ being different from $CR^1$. More preferably, $X^6$ is $CR^1$ and optionally one of $X^5$ and $X^7$ is also $CR^1$. If only one of groups $X^4$, $X^5$, $X^6$ and $X^7$ is $CR^1$, it is preferred that one of $X^5$, $X^6$ and $X^7$ is the group $CR^1$. More preferably, either $X^5$ or $X^6$ is the group $CR^1$. In particular, $X^6$ is the group $CR^1$.

In an alternatively preferred embodiment of the invention, the heteroaromatic ring G carries a substituent $R^1$. In this case it is preferred that none of $X^4$, $X^5$, $X^6$ and $X^7$ is $CR^1$.

In a preferred embodiment of the invention, the mandatorily present nitrogen ring atom of the bicyclic heteroaromatic moiety is in the position of $X^1$, $X^2$ or $X^3$. Thus, at least one, preferably one or two of $X^1$, $X^2$ and $X^3$ are N and $X^4$, $X^5$, $X^6$ and $X^7$ have one of the meanings given above. Preferably, at least one, preferably one or two of $X^1$, $X^2$ and $X^3$ are N and optionally one of $X^4$, $X^5$, $X^6$ and $X^7$ is N, too.

In one preferred embodiment of the invention, $X^1$ is N, one of the groups $X^2$ and $X^3$ is $CR^2$ and the other is $CR^2$ or N and one of the groups $X^4$, $X^5$, $X^6$ and $X^7$ is $CR^1$, $CR^3$ or N and the other three groups are $CR^1$ or $CR^3$. More preferably, $X^1$ is N, $X^2$ and $X^3$ are $CR^2$ and one of the groups $X^4$, $X^5$, $X^6$ and $X^7$ is $CR^1$, $CR^3$ or N and the other three groups are $CR^1$ or $CR^3$.

Even more preferably, $X^1$ is N, $X^4$ is $CR^1$, $CR^3$ or N, $X^2$ and $X^3$ are $CR^2$ and $X^5$, $X^6$ and $X^7$ are $CR^1$ or $CR^3$. In all these combinations of $X^1$ to $X^7$ it is preferred that one or two, preferably one of $X^4$, $X^5$, $X^6$ and $X^7$ is $CR^1$. Particularly preferably $X^6$ is $CR^1$. Alternatively, none of $X^4$, $X^5$, $X^6$ and $X^7$ is $CR^1$ and G carries one substituent $R^1$ and optionally 1, 2 or 3 substituents $R^5$.

In an alternatively preferred embodiment of the invention, $X^2$ is N, one of the groups $X^1$ and $X^3$ is $CR^2$ and the other is $CR^2$ or N and one of the groups $X^4$, $X^5$, $X^6$ and $X^7$ is $CR^1$, $CR^3$ or N and the other three groups are $CR^1$ or $CR^3$. More preferably, $X^2$ is N, $X^1$ and $X^3$ are $CR^2$ and one of the groups $X^4$, $X^5$, $X^6$ and $X^7$ is $CR^1$, $CR^3$ or N and the other three groups are $CR^1$ or $CR^3$. Even more preferably, $X^2$ is N, $X^4$ is $CR^1$, $CR^3$ or N, $X^1$ and $X^3$ are $CR^2$ and $X^5$, $X^6$ and $X^7$ are $CR^1$ or $CR^3$. In all these combinations of $X^1$ to $X^7$ it is preferred that one or two, preferably one of $X^4$, $X^5$, $X^6$ and $X^7$ is $CR^1$. Particularly preferably $X^6$ is $CR^1$. Alternatively, none of $X^4$, $X^5$, $X^6$ and $X^7$ is $CR^1$ and G carries one substituent $R^1$ and optionally 1, 2 or 3 substituents $R^5$.

In an alternatively preferred embodiment of the invention, $X^3$ is N, one of the groups $X^1$ and $X^2$ is $CR^2$ and the other is $CR^2$ or N and one of the groups $X^4$, $X^5$, $X^6$ and $X^7$ is $CR^1$, $CR^3$ or N and the other three groups are $CR^1$ or $CR^3$. More preferably, $X^3$ is N, $X^1$ and $X^2$ are $CR^2$ and one of the groups $X^4$, $X^5$, $X^6$ and $X^7$ is $CR^1$, $CR^3$ or N and the other three groups are $CR^1$ or $CR^3$. Even more preferably, $X^3$ is N, $X^4$ is $CR^1$, $CR^3$ or N, $X^1$ and $X^2$ are $CR^2$ and $X^5$, $X^6$ and $X^7$ are $CR^1$ or $CR^3$. In all these combinations of $X^1$ to $X^7$ it is preferred that one or two, preferably one of $X^4$, $X^5$, $X^6$ and $X^7$ is $CR^1$. Particularly preferably $X^6$ is $CR^1$. Alternatively, none of $X^4$, $X^5$, $X^6$ and $X^7$ is $CR^1$ and G carries one substituent $R^1$ and optionally 1, 2 or 3 substituents $R^5$.

However, the first embodiment, wherein $X^1$ is N, is more preferred. Accordingly, in a more preferred embodiment of the invention, $X^1$ is N, one of the groups $X^2$ and $X^3$ is $CR^2$ and the other is $CR^2$ or N and one of the groups $X^4$, $X^5$, $X^6$ and $X^7$ is $CR^1$, $CR^3$ or N and the other three groups are $CR^1$ or $CR^3$; even more preferably, $X^1$ is N, $X^2$ and $X^3$ are $CR^2$ and one of the groups $X^4$, $X^5$, $X^6$ and $X^7$ is $CR^1$, $CR^3$ or N and the other three groups are $CR^1$ or $CR^3$; and in particular, $X^1$ is N, $X^4$ is $CR^1$, $CR^3$ or N, $X^2$ and $X^3$ are $CR^2$ and $X^5$, $X^6$ and $X^7$ are $CR^1$ or $CR^3$. In all these combinations of $X^1$ to $X^7$ it is preferred that one or two, preferably one of $X^4$, $X^5$, $X^6$ and $X^7$ is $CR^1$. Particularly preferably $X^5$ or $X^6$ is $CR^1$. Alternatively, none of $X^4$, $X^5$, $X^6$ and $X^7$ is $CR^1$ and G carries one substituent $R^1$ and optionally 1, 2 or 3 substituents $R^5$. Specifically, $X^1$ is N, $X^2$ and $X^3$ are $CR^2$, preferably CH, one of $X^5$ and $X^6$ is $CR^1$ and the other is $CR^3$, preferably CH, $X^4$ and $X^7$ are $CR^3$, preferably CH, and G carries no substituent $R^1$ (and preferably also no substituent $R^5$); or $X^1$ is N, $X^2$ and $X^3$ are $CR^2$, preferably CH, $X^4$, $X^5$ and $X^7$ are $CR^3$, preferably CH, $X^6$ is $CR^3$, preferably C-methoxy, and G carries one substituent $R^1$ (and preferably no substituent $R^5$).

$R^1$, which is mandatorily present either as substituent of the condensed heteroaromatic ring system or as substituent of G (or of both), is preferably a 7-, 8-, 9- or 10-membered bicyclic saturated heterocyclic ring containing one nitrogen atom and optionally 1, 2 or 3 further heteroatoms, selected from N and O and preferably N, as ring members and optionally carrying 1, 2 or 3 substituents $R^6$ which have one of the general meanings given above or one of the preferred meanings given below. More preferably, $R^1$ is a 7-, 8-, 9- or 10-membered bicyclic saturated heterocyclic ring containing one nitrogen atom and optionally 1 or 2 further heteroatoms, selected from N and O and preferably N, as ring members and optionally carrying 1, 2 or 3 substituents $R^6$ which have one of the general meanings given above or one of the preferred meanings given below. Even more preferably, $R^1$ is a 7-, 8-, 9- or 10-membered bicyclic saturated heterocyclic ring containing one nitrogen atom and optionally 1 further heteroatom, selected from N and O and preferably N, as ring members and optionally carrying 1, 2 or 3 substituents $R^6$ which have one of the general meanings given above or one of the preferred meanings given below.

Examples for preferred radicals $R^1$ have the following formulae

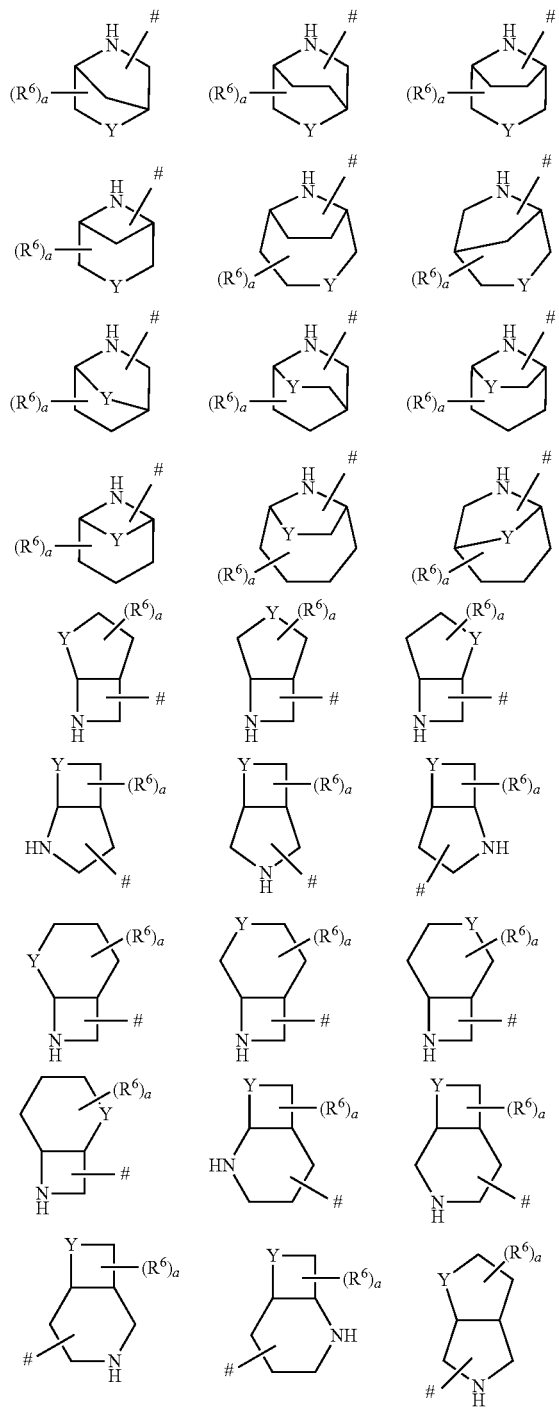

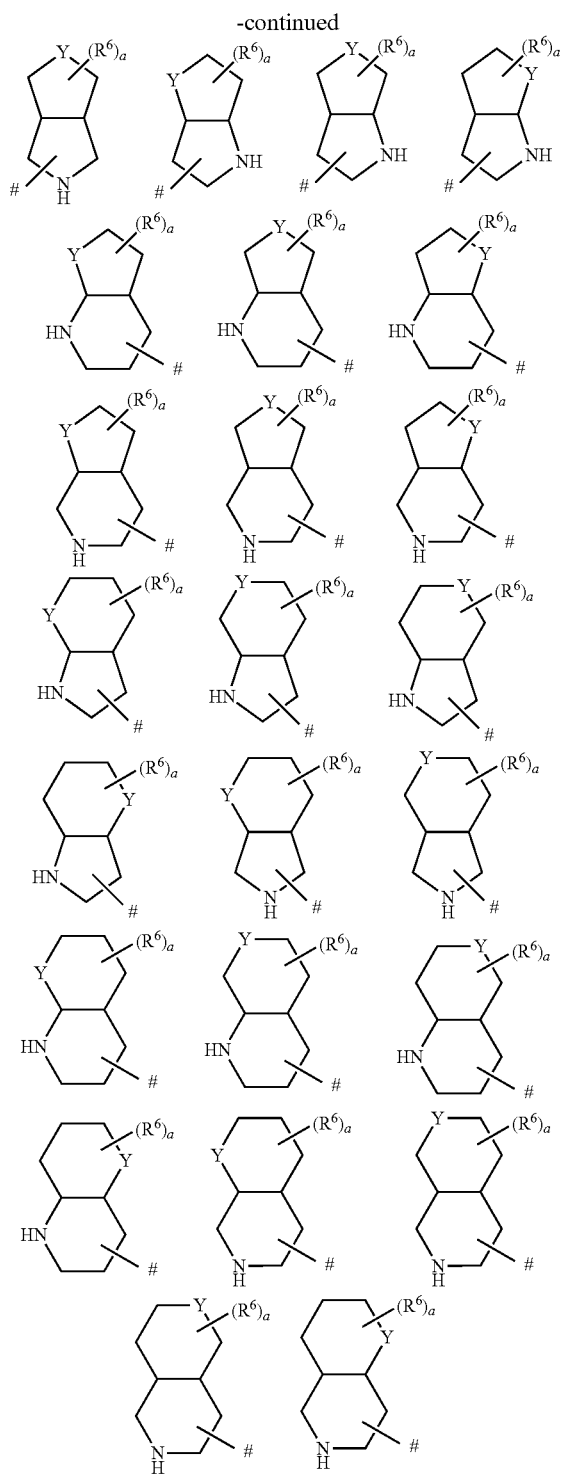

where
Y is $CH_2$, NH or O, preferably NH or O and more preferably NH;
$R^6$ has one of the general meanings given above or one of the preferred meanings given below;
a is 0, 1, 2 or 3, preferably 0, 1 or 2 and more preferably 0 or 1; and
# is the attachment point to the remainder of the molecule.
$R^6$ and/or the attachment point can also be located on a nitrogen atom where they replace the hydrogen atom. $R^6$ and the attachment point can also be located on the same ring or be switched in the above formulae. However, they are preferably located on different rings and as shown above. Preferably, the attachment point is located on a nitrogen atom. $R^6$, if present, is preferably also located on a nitrogen atom.

More preferably, $R^1$ is a 7-, 8-, 9- or 10-membered bicyclic saturated heterocyclic ring bound via a nitrogen ring atom, optionally containing one further heteroatom, selected from N and O and preferably N, as ring member and optionally carrying 1, 2 or 3, preferably 1 or 2 and more preferably 1 substituents $R^6$ which have one of the general meanings given above or one of the preferred meanings given below.

Even more preferably, $R^1$ is selected from one of the following formulae

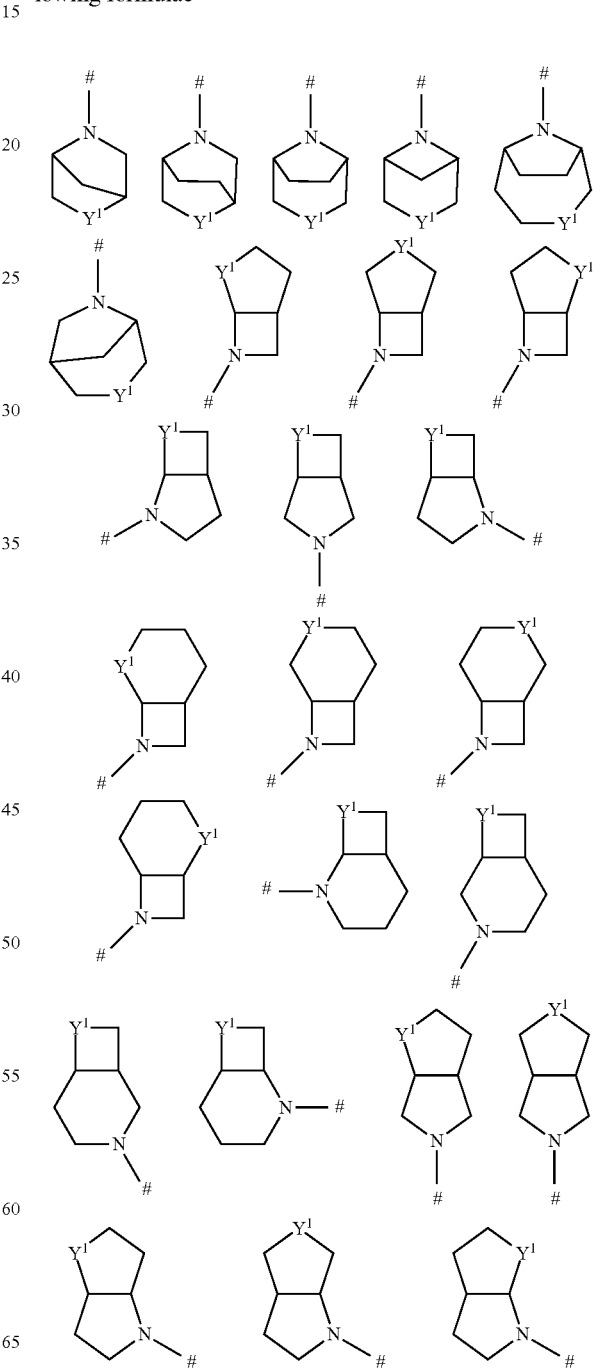

-continued

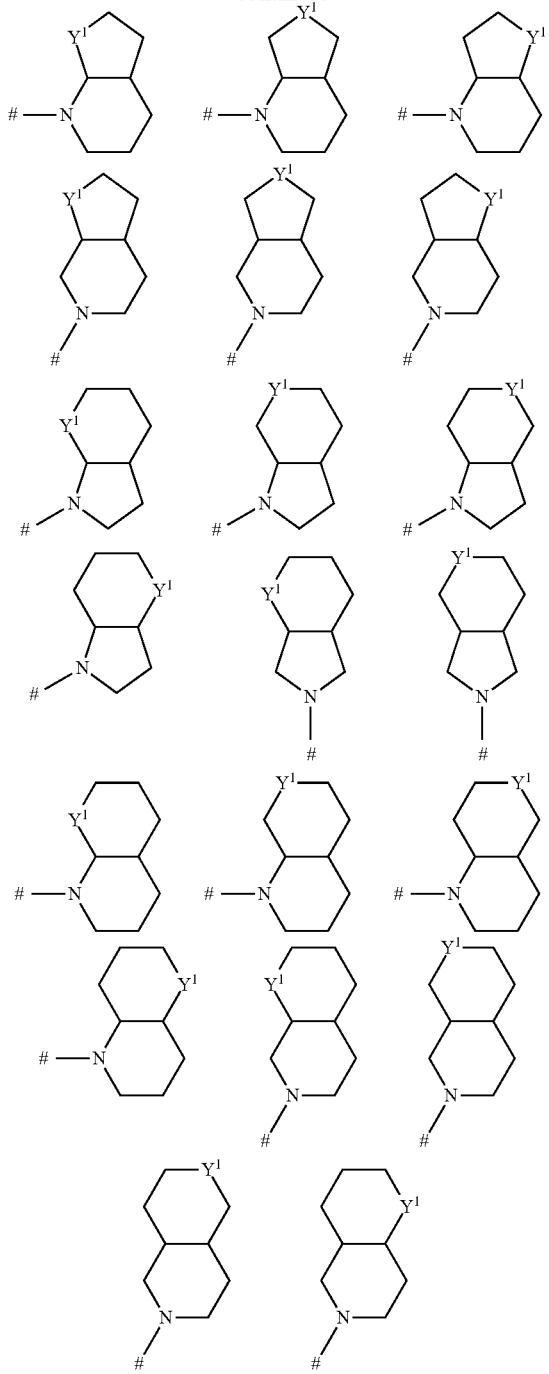

where
Y$^1$ is CH$_2$, O or NR$^{61}$, preferably O or NR$^{61}$ and more preferably NR$^{61}$;
R$^{61}$ is H or has one of the general meanings of R$^6$ given above or one of the preferred meanings given below; and
# is the attachment point to the remainder of the molecule.

Especially preferably, R$^1$ is a 7-, 8-, 9- or 10-membered bicyclic saturated heterocyclic ring bound via a nitrogen ring atom, containing one further heteroatom, selected from N and O and preferably N, as ring member and optionally carrying 1, 2 or 3, preferably 1 or 2 and more preferably 1 substituents R$^6$ which have one of the general meanings given above or one of the preferred meanings given below.

Particularly, R$^1$ is selected from one of the following formulae

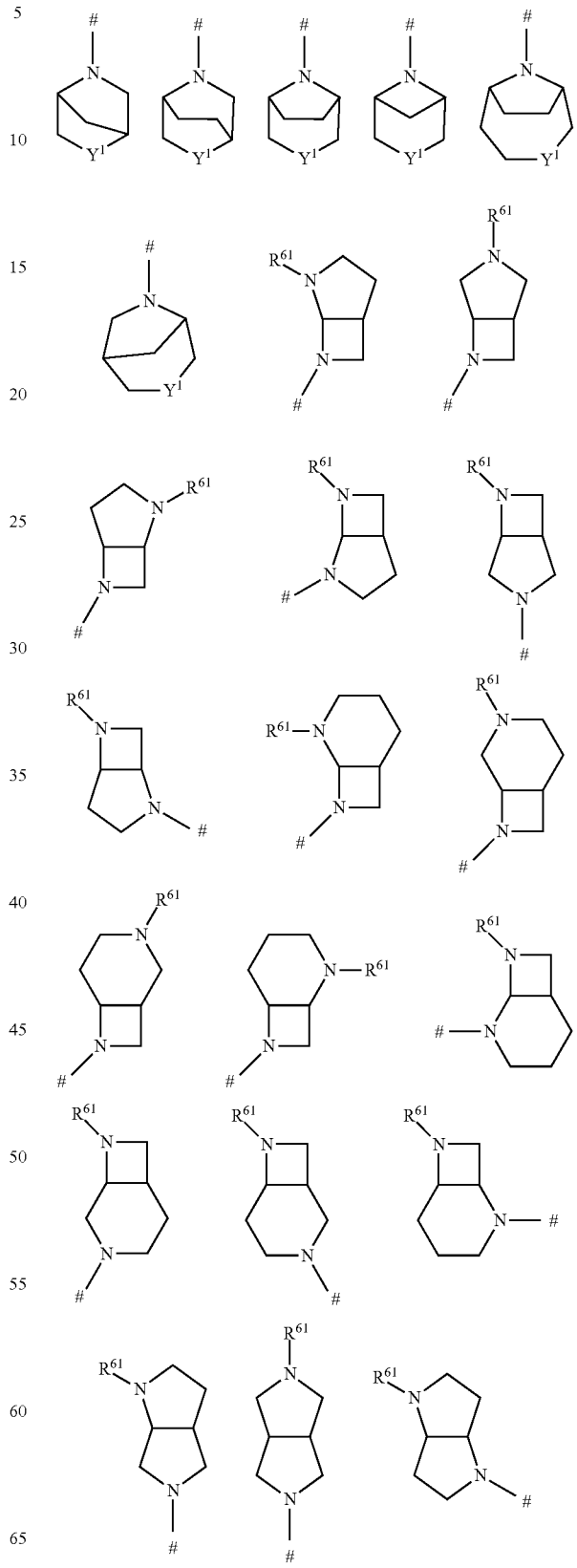

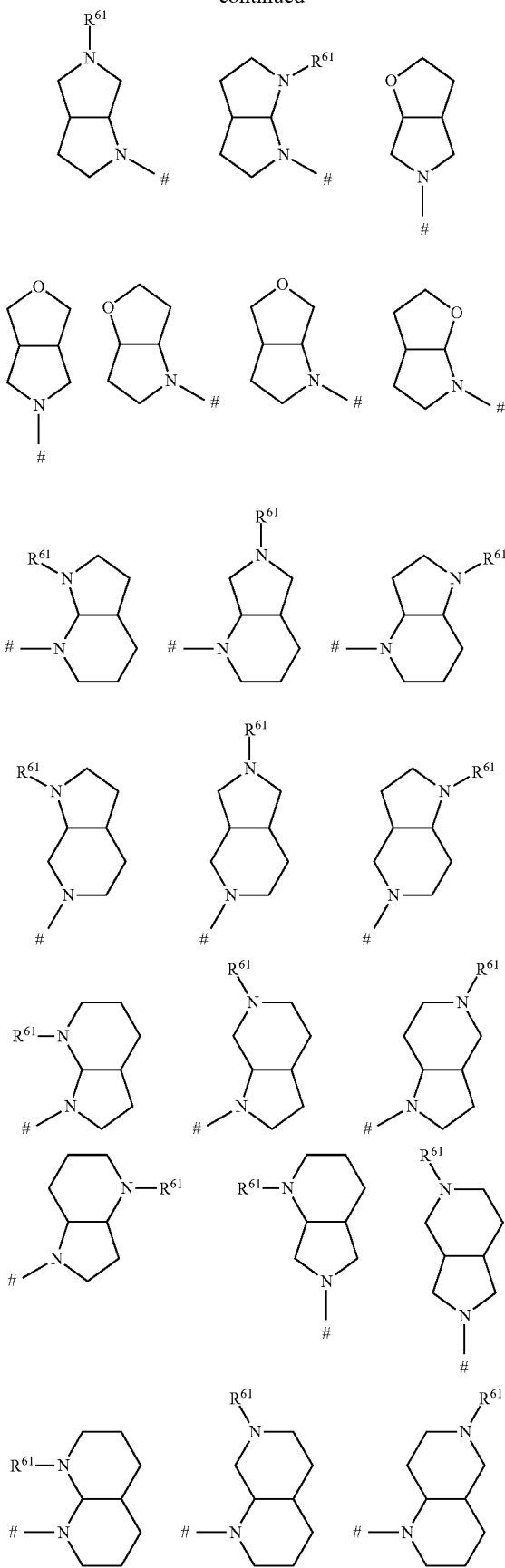

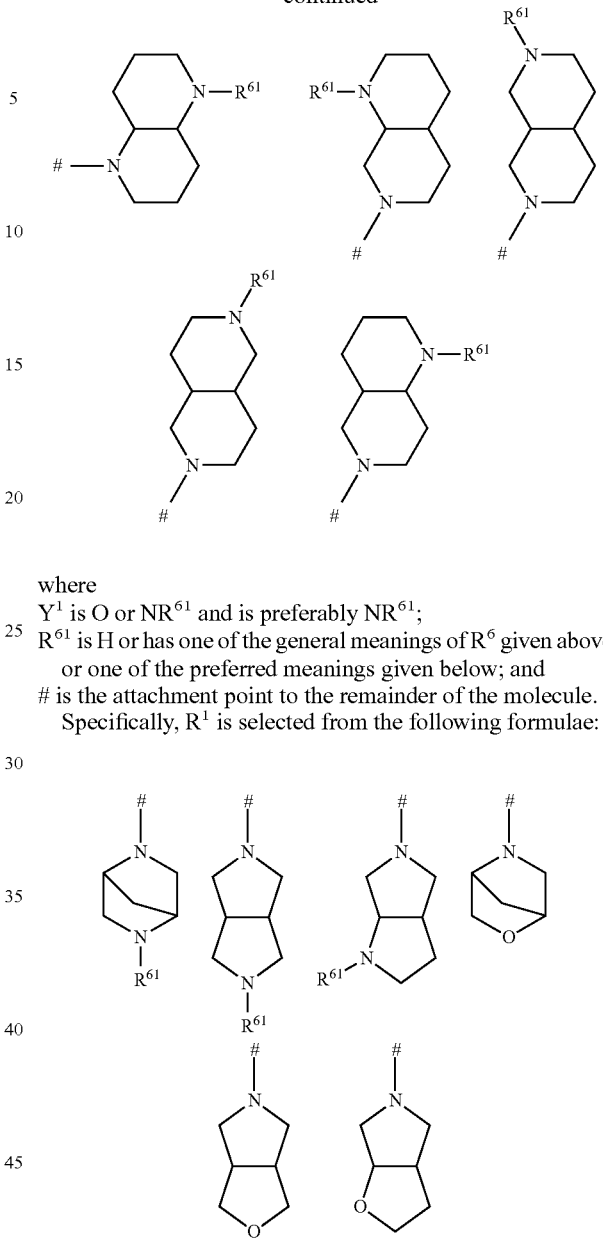

where
Y¹ is O or NR⁶¹ and is preferably NR⁶¹;
R⁶¹ is H or has one of the general meanings of R⁶ given above or one of the preferred meanings given below; and
# is the attachment point to the remainder of the molecule.

Specifically, R¹ is selected from the following formulae:

where
R⁶¹ is H or has one of the general meanings of R⁶ given above or one of the preferred meanings given below; and
# is the attachment point to the remainder of the molecule.

Preferably, R⁶ is selected from $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylcarbonyl, $C_1$-$C_4$-fluoroalkylcarbonyl, $C_1$-$C_4$-alkoxycarbonyl, $C_1$-$C_4$-fluoroalkoxycarbonyl and benzyl. More preferably, R⁶ is selected from $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylcarbonyl, $C_1$-$C_4$-fluoroalkylcarbonyl, $C_1$-$C_4$-alkoxycarbonyl and $C_1$-$C_4$-fluoroalkoxycarbonyl. Even more preferably, R⁶ is selected from $C_1$-$C_4$-alkyl, $C_1$-$C_4$-fluoroalkyl, $C_1$-$C_4$-alkoxycarbonyl and $C_1$-$C_4$-fluoroalkoxycarbonyl and in particular from $C_1$-$C_4$-alkyl and $C_1$-$C_4$-alkoxycarbonyl. Specifically, R⁶ is $C_1$-$C_4$-alkoxycarbonyl.

Accordingly, R⁶¹ in the above formulae is preferably selected from hydrogen, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylcarbonyl, $C_1$-$C_4$-fluoroalkylcarbonyl, $C_1$-$C_4$-alkoxycarbonyl, $C_1$-$C_4$-fluoroalkoxycarbonyl and benzyl. More preferably, $R^{61}$ is selected from hydrogen, $C_1$-$C_4$-alkyl, $C_1$-$C_4$-fluoroalkyl, $C_1$-$C_4$-alkoxy, $C_1$-$C_4$-fluoroalkoxy, $C_1$-$C_4$-alkylcarbonyl, $C_1$-$C_4$-fluoroalkylcarbonyl, $C_1$-$C_4$-alkoxycarbonyl and $C_1$-$C_4$-fluoroalkoxycarbonyl. Even more preferably, $R^{61}$ is selected from hydrogen, $C_1$-$C_4$-alkyl, $C_1$-$C_4$-fluoroalkyl, $C_1$-$C_4$-alkoxycarbonyl and $C_1$-$C_4$-fluoroalkoxycarbonyl and in particular from hydrogen, $C_1$-$C_4$-alkyl and $C_1$-$C_4$-alkoxycarbonyl. Specifically, $R^{61}$ is hydrogen or $C_1$-$C_4$-alkoxycarbonyl.

Preferably, one of all radicals $R^3$ present in the compound I has one of the general meanings given above or one of the preferred meaning given below and the other radicals $R^3$ present in compound I are all hydrogen; i.e. it is preferred that at most one of $X^4$, $X^5$, $X^6$ and $X^7$ is $CR^3$ with $R^3$ being different from hydrogen.

Preferably, each $R^3$ is independently selected from hydrogen, halogen, $C_1$-$C_4$-alkyl, $C_1$-$C_4$-fluoroalkyl, $C_1$-$C_4$-alkoxy and $C_1$-$C_4$-fluoroalkoxy, and specifically from hydrogen and $C_1$-$C_4$-alkoxy. It is preferred that at most one of $X^4$, $X^5$, $X^6$ and $X^7$ is $CR^3$ with $R^3$ being different from hydrogen. If one or two of $X^4$, $X^5$, $X^6$ and $X^7$ is $CR^1$, $R^3$ is specifically hydrogen.

If none $X^4$, $X^5$, $X^6$ and $X^7$ of is $CR^1$, it is preferred that one $R^3$ is different from hydrogen.

Preferably, each $R^2$ is independently selected from hydrogen, halogen, $C_1$-$C_4$-alkyl and $C_1$-$C_4$-fluoroalkyl. It is preferred that at most one of $X^1$, $X^2$ and $X^3$ is $CR^2$ with $R^2$ being different from hydrogen. Accordingly, in a preferred embodiment one of groups $X^1$, $X^2$ and $X^3$ is N, one of groups $X^1$, $X^2$ and $X^3$ is CH and one of groups $X^1$, $X^2$ and $X^3$ is $CR^2$, where $R^2$ has one of the meanings given above. Specifically, all radicals $R^2$ are hydrogen.

The heteroaromatic group G is preferably a 6-membered heteroaromatic ring having 1, 2 or 3, preferably 1 or 2 nitrogen ring atoms and is bonded in α-position to one of these nitrogen atoms. Preferably G is selected from pyridin-2-yl, pyrazin-2-yl, pyrimidin-2-yl, pyrimidin-4-yl, pyridazin-3-yl and triazin-2-yl, which may carry 1, 2, or 3 substituents $R^5$ or which may carry 1 or 2 substituents $R^5$ and one substituent $R^1$, where each $R^5$ independently has one of the general meanings given above or one of the preferred meanings given below and $R^1$ has one of the general or preferred meanings given above.

More preferably, G is selected from pyridin-2-yl and pyrazin-2-yl, which may carry 1, 2, or 3 substituents $R^5$ or which may carry 1 or 2 substituents $R^5$ and one substituent $R^1$, where each $R^5$ independently has one of the general meanings given above or one of the preferred meanings given below and $R^1$ has one of the general or preferred meanings given above. Specifically, G is pyrazin-2-yl which may carry 1, 2, or 3 substituents $R^5$ or which may carry 1 or 2 substituents $R^5$ and one substituent $R^1$, where each $R^5$ independently has one of the general meanings given above or one of the preferred meanings given below and $R^1$ has one of the general or preferred meanings given above.

If G is substituted, it carries preferably only one substituent selected from $R^5$ and $R^1$. Preferably, G is substituted by $R^1$ only in case that none of $X^4$, $X^5$, $X^6$ and $X^7$ is $CR^1$.

Preferred substituents $R^5$ are selected from halogen, $C_1$-$C_4$-alkyl, $C_1$-$C_4$-fluoroalkyl, $C_1$-$C_4$-alkoxy, $C_1$-$C_4$-fluoroalkoxy and a group $NR^aR^b$, where $R^a$ and $R^b$ have one of the meanings given above. When $R^5$ represents a group $NR^aR^b$, it is preferred that $R^a$ and $R^b$, together with the nitrogen atom to which they are bonded, form a 3-, 4-, 5- or 6-membered N-bound saturated heterocyclic ring which may contain a further heteroatom as ring member selected from N and O, such as in aziridin-1-yl, azetidin-1-yl, pyrrolidin-1-yl, pyrazolidin-1-yl, imidazolidin-1-yl, oxazolidin-3-yl, isoxazolidin-2-yl, [1,2,3]-triazolidin-1-yl, [1,2,3]-triazolidin-2-yl, [1,2,4]-triazolidin-1-yl, [1,2,4]-triazolidin-4-yl, piperidin-1-yl, piperazin-1-yl and morpholin-4-yl. Specifically, $R^5$ is $C_1$-$C_4$-fluoroalkyl and more specifically $CF_3$.

Preferably, G is unsubstituted if one or two of $X^4$, $X^5$, $X^6$ and $X^7$ are $CR^1$; and carries one substituent $R^1$ and no substituent $R^5$ if none of $X^4$, $X^5$, $X^6$ and $X^7$ is $CR^1$. In the latter case, $R^1$ is preferably bound on the 6-position, relative to the 1-position of the nitrogen ring atom and to the 2-position of the attachment point of G to the group $NR^4$.

In group A, $R^{A1}$ and $R^{A2}$ are preferably selected from hydrogen, $C_1$-$C_2$-alkyl, $C_1$-$C_2$-fluoroalkyl, $NH_2$ and OH, more preferably from hydrogen, $C_1$-$C_2$-alkyl and $C_1$-$C_2$-fluoroalkyl and are specifically both H.

In group A, $R^B$ is preferably selected from hydrogen, methyl and ethyl and more preferably from hydrogen and methyl. Specifically, $R^B$ is hydrogen.

A is preferably selected from $CH_2$, NH or $NCH_3$ and more preferably from NH or $NCH_3$. Specifically, A is NH.

$R^4$ is preferably selected from hydrogen, methyl and ethyl and more preferably from hydrogen and methyl. Specifically, $R^4$ is hydrogen.

Particularly preferred compounds are compounds of formula I, the stereoisomers, prodrugs, tautomers and/or physiologically tolerated acid addition salts thereof, wherein A is selected from the group consisting of $CH_2$, NH and $NCH_3$, and is preferably NH;

$X^1$ is N;

$X^2$ and $X^3$ are independently of each $CR^2$;

$X^4$ is selected from the $CR^3$ and N, and is preferably $CR^3$;

$X^5$, $X^6$ and $X^7$ are independently of each other selected from the group consisting of $CR^1$, $CR^3$;
  with the proviso that only one of $X^5$, $X^6$ and $X^7$ is $CR^1$, it being preferred that $X^6$ is $CR^1$ and $X^5$ and $X^7$ are $CR^3$ or that $X^5$ is $CR^1$ and $X^6$ and $X^7$ are $CR^3$;

G is a 6-membered heteroaromatic ring selected from pyridin-2-yl, pyrazin-2-yl, pyrimidin-2-yl, pyrimidin-4-yl, pyridazin-3-yl and triazin-2-yl, which may carry 1, 2, or 3 substituents $R^5$;

$R^1$ is a 7-, 8-, 9- or 10-membered bicyclic saturated heterocyclic ring bound via a nitrogen ring atom, optionally containing one further heteroatom selected from N and O as ring member and optionally carrying 1, 2 or 3 substituents $R^6$;

each $R^2$ is independently selected from the group consisting of hydrogen, OH, halogen, CN, $C_1$-$C_6$-alkyl, $C_1$-$C_6$-haloalkyl and $NR^aR^b$ and is preferably hydrogen;

one $R^3$ is selected from the group consisting of hydrogen, halogen, $C_1$-$C_4$-alkyl, $C_1$-$C_4$-fluoroalkyl, $C_1$-$C_4$-alkoxy and $C_1$-$C_4$-fluoroalkoxy and preferably from hydrogen, $C_1$-$C_4$-alkoxy and $C_1$-$C_4$-fluoroalkoxy and the other radicals $R^3$ are hydrogen;

$R^4$ is selected from the group consisting of hydrogen, methyl and ethyl, preferably hydrogen and methyl and is specifically hydrogen;

$R^5$ and $R^7$, independently of each other and independently of each occurrence, have one of the meanings given here for $R^3$ and are preferably hydrogen and $R^5$ is preferably also $CF_3$;

$R^6$ is selected from hydrogen, $C_1$-$C_4$-alkoxycarbonyl and $C_1$-$C_4$-fluoroalkoxycarbonyl; and $R^a$ and $R^b$ are independently of each other selected from the group consisting of hydrogen, $C_1$-$C_6$-alkyl, $C_1$-$C_4$-haloalkyl and $C_1$-$C_4$-alkoxy;

or $R^a$ and $R^b$ form, together with the nitrogen atom to which they are bonded, a 3-, 4-, 5- or 6-membered saturated or N-heterocyclic ring, which may contain 1 further heteroatom selected from the group consisting of O and N as a ring member.

Alternatively, particularly preferred compounds are compounds of formula I, the stereoisomers, prodrugs, tautomers and/or physiologically tolerated acid addition salts thereof, wherein A is selected from the group consisting of $CH_2$, NH and $NCH_3$, and is preferably NH;

$X^1$ is N;

$X^2$ and $X^3$ are independently of each other $CR^2$;

$X^4$ is selected from the $CR^3$ and N, and is preferably $CR^3$;

$X^5$, $X^6$ and $X^7$ are independently of each other $CR^3$;

G is a 6-membered heteroaromatic ring selected from pyridin-2-yl, pyrazin-2-yl, pyrimidin-2-yl, pyrimidin-4-yl, pyridazin-3-yl and triazin-2-yl, which carries one radical $R^1$ and which may further carry 1 or 2 substituents $R^5$;

$R^1$ is a 7-, 8-, 9- or 10-membered bicyclic saturated heterocyclic ring bound via a nitrogen ring atom, optionally containing one further heteroatom selected from N and O as ring member and optionally carrying 1, 2 or 3 substituents $R^6$;

each $R^2$ is independently selected from the group consisting of hydrogen, OH, halogen, CN, $C_1$-$C_6$-alkyl, $C_1$-$C_6$-haloalkyl and $NR^aR^b$ and is preferably hydrogen;

one $R^3$ is selected from the group consisting of hydrogen, halogen, $C_1$-$C_4$-alkyl, $C_1$-$C_4$-fluoroalkyl, $C_1$-$C_4$-alkoxy and $C_1$-$C_4$-fluoroalkoxy and preferably from hydrogen, $C_1$-$C_4$-alkoxy and $C_1$-$C_4$-fluoroalkoxy and the other radicals $R^3$ are hydrogen;

$R^4$ is selected from the group consisting of hydrogen, methyl and ethyl, preferably hydrogen and methyl and is specifically hydrogen;

$R^5$ and $R^7$, independently of each other and independently of each occurrence, have one of the meanings given here for $R^3$ and are preferably hydrogen;

$R^6$ is selected from hydrogen, $C_1$-$C_4$-alkoxycarbonyl and $C_1$-$C_4$-fluoroalkoxycarbonyl; and $R^a$ and $R^b$ are independently of each other selected from the group consisting of hydrogen, $C_1$-$C_6$-alkyl, $C_1$-$C_4$-haloalkyl and $C_1$-$C_4$-alkoxy;

or $R^a$ and $R^b$ form, together with the nitrogen atom to which they are bonded, a 3-, 4-, 5- or 6-membered saturated or N-heterocyclic ring, which may contain 1 further heteroatom selected from the group consisting of O and N as a ring member.

Specifically preferred compounds I are those of formulae I.1 to I.26, the stereoisomers, prodrugs, tautomers and/or physiologically tolerated acid addition salts thereof, wherein $R^1$ and $R^3$ have the above-defined general or preferred meanings. Particularly preferred meanings of $R^1$ and $R^3$ in compounds of formula I and specifically in compounds of formulae I.1 to I.26 are as defined below.

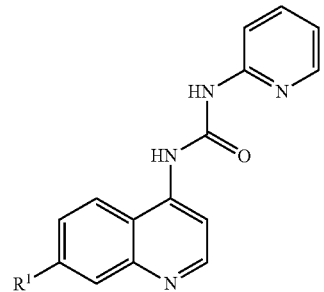

I.1

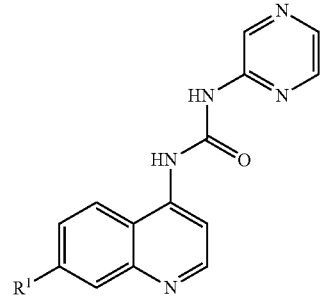

I.2

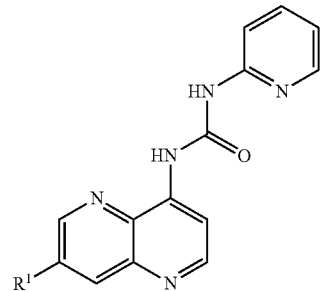

I.3

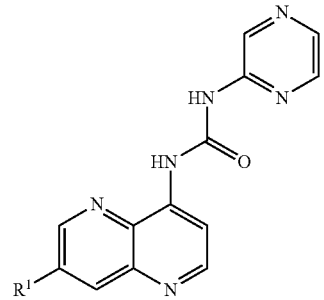

I.4

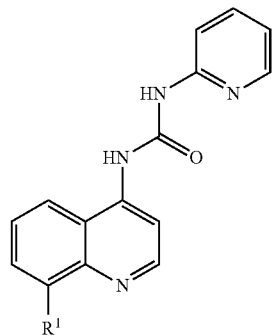

I.5

-continued

I.6

I.7

I.8

I.9

I.10

-continued

I.11

I.12

I.13

I.14

I.15

-continued
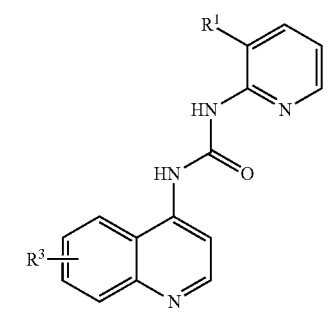
I.16
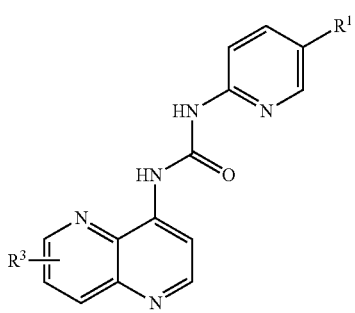
I.21
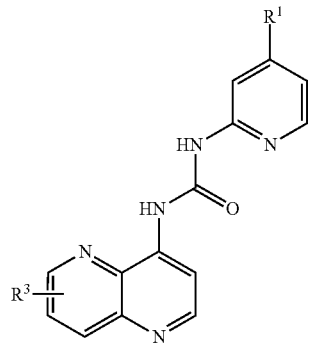
I.17
I.22
I.18
I.23
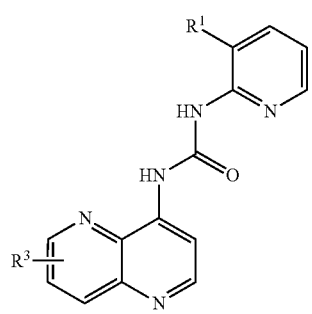
I.19
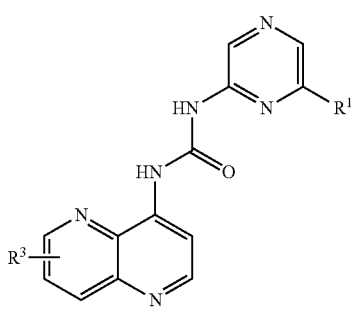
I.24
I.20
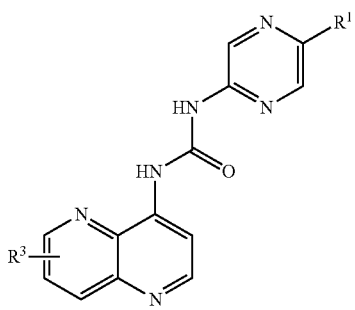
I.25

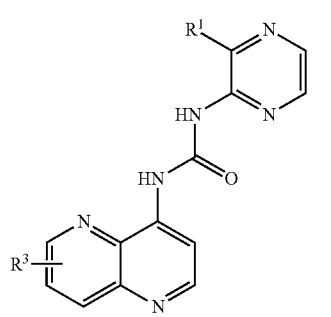
I.26
The pyrazine or pyridine substituents G in compounds I.1 to I.12 may also carry a CF₃ substituent.
Preferred groups $R^1$ in compounds I and specifically in compounds of formulae I.1 to I.26 are selected from the radicals of the following formulae:
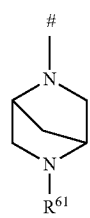
a
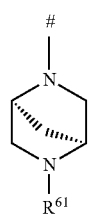
b
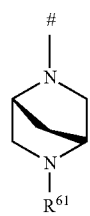
c
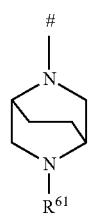
d
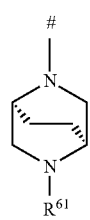
e
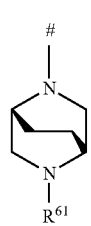
f
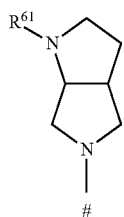
g
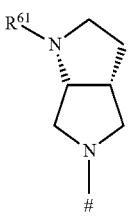
h
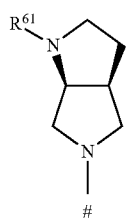
i
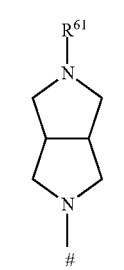
j
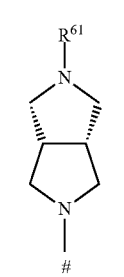
k

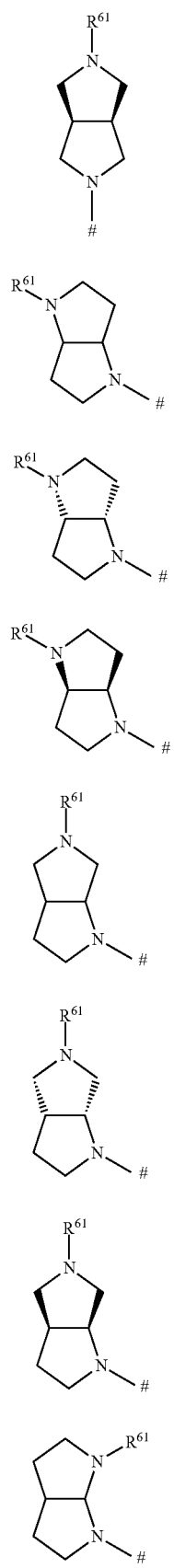
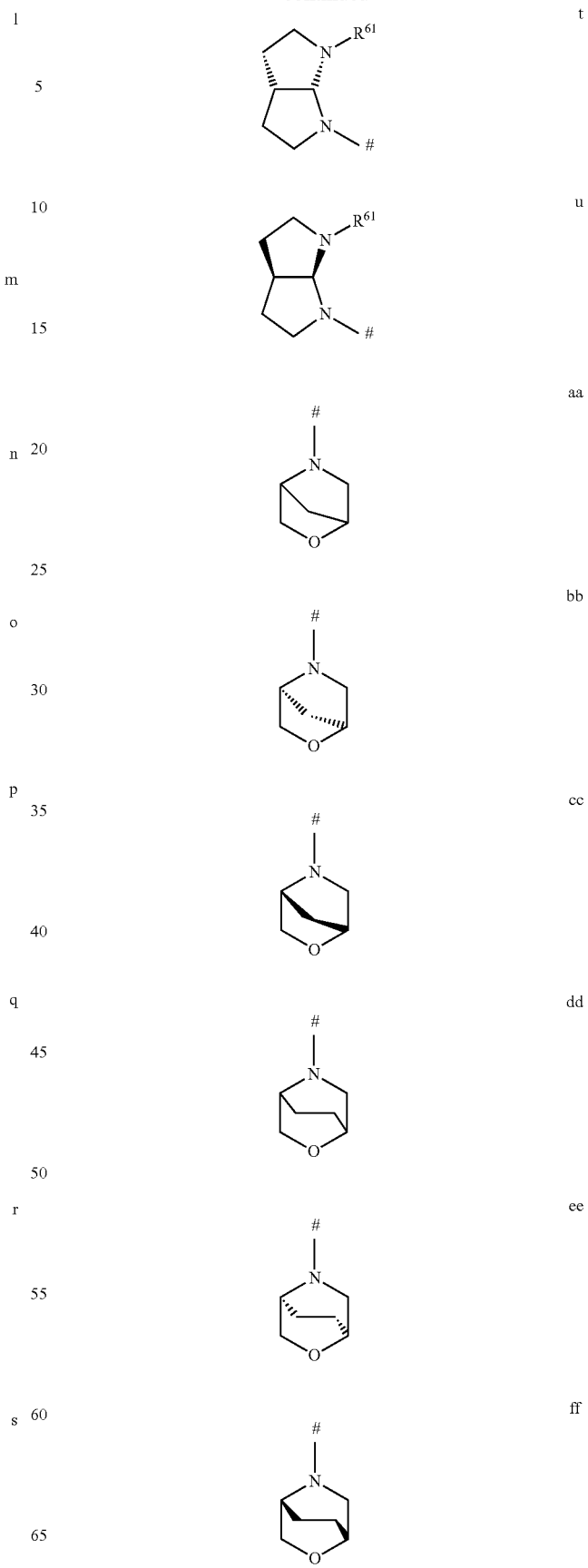

-continued gg 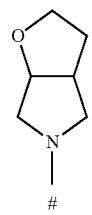

hh 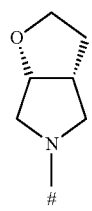

ii 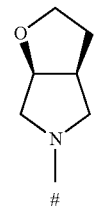

jj 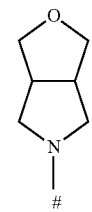

kk 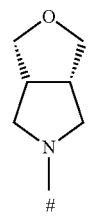

ll 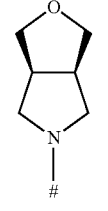

mm 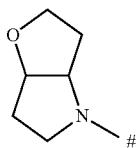

-continued nn 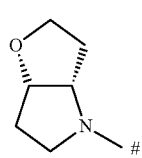

oo 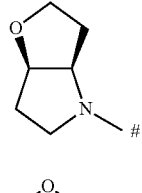

pp 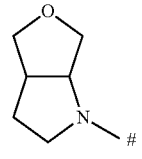

qq 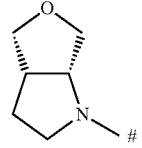

rr 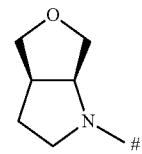

ss 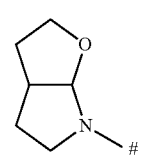

tt 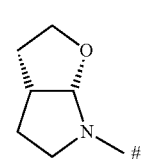

uu 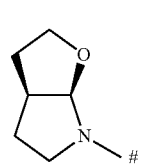

wherein $R^{61}$ is H or has one of the preferred meanings given for $R^6$. "Normal" bonds in positions where they replace wedge or dotted bonds of neighbouring radicals symbolize all possible stereoisomers and mixtures of the respective stereoisomers.

Examples of preferred compounds which are represented by the formulae I.1 to I.26 are listed in following tables 1 to 17724. In the tables, the position of $R^3$ is characterized as follows:

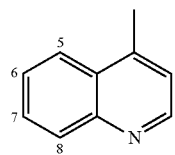

Table 1
Compounds of the formula I.1 in which $R^1$ is a group of formula a and $R^{61}$ is selected from H, methyl, ethyl, n-propyl, isopropyl, n-butyl, sec-butyl, isobutyl, tert-butyl, methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl Table 2
Compounds of the formula I.1 in which $R^1$ is a group of formula b and $R^{61}$ has one of the meanings given in table 1

Table 3
Compounds of the formula I.1 in which $R^1$ is a group of formula c and $R^{61}$ has one of the meanings given in table 1

Table 4
Compounds of the formula I.1 in which $R^1$ is a group of formula d and $R^{61}$ has one of the meanings given in table 1

Table 5
Compounds of the formula I.1 in which $R^1$ is a group of formula e and $R^{61}$ has one of the meanings given in table 1

Table 6
Compounds of the formula I.1 in which $R^1$ is a group of formula f and $R^{61}$ has one of the meanings given in table 1

Table 7
Compounds of the formula I.1 in which $R^1$ is a group of formula g and $R^{61}$ has one of the meanings given in table 1

Table 8
Compounds of the formula I.1 in which $R^1$ is a group of formula h and $R^{61}$ has one of the meanings given in table 1

Table 9
Compounds of the formula I.1 in which $R^1$ is a group of formula i and $R^{61}$ has one of the meanings given in table 1

Table 10
Compounds of the formula I.1 in which $R^1$ is a group of formula j and $R^{61}$ has one of the meanings given in table 1

Table 11
Compounds of the formula I.1 in which $R^1$ is a group of formula k and $R^{61}$ has one of the meanings given in table 1

Table 12
Compounds of the formula I.1 in which $R^1$ is a group of formula l and $R^{61}$ has one of the meanings given in table 1

Table 13
Compounds of the formula I.1 in which $R^1$ is a group of formula m and $R^{61}$ has one of the meanings given in table 1

Table 14
Compounds of the formula I.1 in which $R^1$ is a group of formula n and $R^{61}$ has one of the meanings given in table 1

Table 15
Compounds of the formula I.1 in which $R^1$ is a group of formula o and $R^{61}$ has one of the meanings given in table 1

Table 16
Compounds of the formula I.1 in which $R^1$ is a group of formula p and $R^{61}$ has one of the meanings given in table 1

Table 17
Compounds of the formula I.1 in which $R^1$ is a group of formula q and $R^{61}$ has one of the meanings given in table 1

Table 18
Compounds of the formula I.1 in which $R^1$ is a group of formula r and $R^{61}$ has one of the meanings given in table 1

Table 19
Compounds of the formula I.1 in which $R^1$ is a group of formula s and $R^{61}$ has one of the meanings given in table 1

Table 20
Compounds of the formula I.1 in which $R^1$ is a group of formula t and $R^{61}$ has one of the meanings given in table 1

Table 21
Compounds of the formula I.1 in which $R^1$ is a group of formula u and $R^{61}$ has one of the meanings given in table 1

Table 22
Compounds of the formula I.1 in which $R^1$ is a group of formula aa

Table 23
Compounds of the formula I.1 in which $R^1$ is a group of formula bb

Table 24
Compounds of the formula I.1 in which $R^1$ is a group of formula cc

Table 25
Compounds of the formula I.1 in which $R^1$ is a group of formula dd

Table 26
Compounds of the formula I.1 in which $R^1$ is a group of formula ee

Table 27
Compounds of the formula I.1 in which $R^1$ is a group of formula ff

Table 28
Compounds of the formula I.1 in which $R^1$ is a group of formula gg

Table 29
Compounds of the formula I.1 in which $R^1$ is a group of formula hh

Table 30
Compounds of the formula I.1 in which $R^1$ is a group of formula ii

Table 31
Compounds of the formula I.1 in which $R^1$ is a group of formula jj

Table 32
Compounds of the formula I.1 in which $R^1$ is a group of formula kk

Table 33
Compounds of the formula I.1 in which $R^1$ is a group of formula ll

Table 34
Compounds of the formula I.1 in which $R^1$ is a group of formula mm

Table 35
Compounds of the formula I.1 in which $R^1$ is a group of formula nn

Table 36
Compounds of the formula I.1 in which $R^1$ is a group of formula oo

Table 37
Compounds of the formula I.1 in which $R^1$ is a group of formula pp

Table 38
Compounds of the formula I.1 in which $R^1$ is a group of formula qq

Table 39
Compounds of the formula I.1 in which $R^1$ is a group of formula rr

Table 40
Compounds of the formula I.1 in which $R^1$ is a group of formula ss

Table 41
Compounds of the formula I.1 in which $R^1$ is a group of formula tt
Table 42
Compounds of the formula I.1 in which $R^1$ is a group of formula uu
Tables 43 to 84
Compounds of the formula I.2 in which the combination of $R^1$ and $R^{61}$ is as defined in tables 1 to 21 or in which $R^1$ is as defined in tables 22 to 42
Tables 85 to 126
Compounds of the formula I.3 in which the combination of $R^1$ and $R^{61}$ is as defined in tables 1 to 21 or in which $R^1$ is as defined in tables 22 to 42
Tables 127 to 168
Compounds of the formula I.4 in which the combination of $R^1$ and $R^{61}$ is as defined in tables 1 to 21 or in which $R^1$ is as defined in tables 22 to 42
Tables 169 to 210
Compounds of the formula I.5 in which the combination of $R^1$ and $R^{61}$ is as defined in tables 1 to 21 or in which $R^1$ is as defined in tables 22 to 42
Tables 211 to 252
Compounds of the formula I.6 in which the combination of $R^1$ and $R^{61}$ is as defined in tables 1 to 21 or in which $R^1$ is as defined in tables 22 to 42
Tables 253 to 294
Compounds of the formula I.7 in which the combination of $R^1$ and $R^{61}$ is as defined in tables 1 to 21 or in which $R^1$ is as defined in tables 22 to 42
Tables 295 to 336
Compounds of the formula I.8 in which the combination of $R^1$ and $R^{61}$ is as defined in tables 1 to 21 or in which $R^1$ is as defined in tables 22 to 42
Tables 337 to 378
Compounds of the formula I.9 in which the combination of $R^1$ and $R^{61}$ is as defined in tables 1 to 21 or in which $R^1$ is as defined in tables 22 to 42
Tables 379 to 420
Compounds of the formula I.10 in which the combination of $R^1$ and $R^{61}$ is as defined in tables 1 to 21 or in which $R^1$ is as defined in tables 22 to 42
Tables 421 to 462
Compounds of the formula I.11 in which the combination of $R^1$ and $R^{61}$ is as defined in tables 1 to 21 or in which $R^1$ is as defined in tables 22 to 42
Tables 463 to 504
Compounds of the formula I.12 in which the combination of $R^1$ and $R^{61}$ is as defined in tables 1 to 21 or in which $R^1$ is as defined in tables 22 to 42
Tables 505 to 546
Compounds of the formula I.13 in which the combination of $R^1$ and $R^{61}$ is as defined in tables 1 to 21 or in which $R^1$ is as defined in tables 22 to 42 and $R^3$ is H
Tables 547 to 588
Compounds of the formula I.13 in which the combination of $R^1$ and $R^{61}$ is as defined in tables 1 to 21 or in which $R^1$ is as defined in tables 22 to 42 and $R^3$ is 5-methyl
Tables 589 to 630
Compounds of the formula I.13 in which the combination of $R^1$ and $R^{61}$ is as defined in tables 1 to 21 or in which $R^1$ is as defined in tables 22 to 42 and $R^3$ is 6-methyl
Tables 631 to 672
Compounds of the formula I.13 in which the combination of $R^1$ and $R^{61}$ is as defined in tables 1 to 21 or in which $R^1$ is as defined in tables 22 to 42 and $R^3$ is 7-methyl
Tables 673 to 714
Compounds of the formula I.13 in which the combination of $R^1$ and $R^{61}$ is as defined in tables 1 to 21 or in which $R^1$ is as defined in tables 22 to 42 and $R^3$ is 8-methyl
Tables 715 to 756
Compounds of the formula I.13 in which the combination of $R^1$ and $R^{61}$ is as defined in tables 1 to 21 or in which $R^1$ is as defined in tables 22 to 42 and $R^3$ is 5-trifluoromethyl
Tables 757 to 798
Compounds of the formula I.13 in which the combination of $R^1$ and $R^{61}$ is as defined in tables 1 to 21 or in which $R^1$ is as defined in tables 22 to 42 and $R^3$ is 6-trifluoromethyl
Tables 799 to 840
Compounds of the formula I.13 in which the combination of $R^1$ and $R^{61}$ is as defined in tables 1 to 21 or in which $R^1$ is as defined in tables 22 to 42 and $R^3$ is 7-trifluoromethyl
Tables 841 to 882
Compounds of the formula I.13 in which the combination of $R^1$ and $R^{61}$ is as defined in tables 1 to 21 or in which $R^1$ is as defined in tables 22 to 42 and $R^3$ is 8-trifluoromethyl
Tables 883 to 924
Compounds of the formula I.13 in which the combination of $R^1$ and $R^{61}$ is as defined in tables 1 to 21 or in which $R^1$ is as defined in tables 22 to 42 and $R^3$ is 5-methoxy
Tables 925 to 966
Compounds of the formula I.13 in which the combination of $R^1$ and $R^{61}$ is as defined in tables 1 to 21 or in which $R^1$ is as defined in tables 22 to 42 and $R^3$ is 6-methoxy
Tables 967 to 1008
Compounds of the formula I.13 in which the combination of $R^1$ and $R^{61}$ is as defined in tables 1 to 21 or in which $R^1$ is as defined in tables 22 to 42 and $R^3$ is 7-methoxy
Tables 1009 to 1050
Compounds of the formula I.13 in which the combination of $R^1$ and $R^{61}$ is as defined in tables 1 to 21 or in which $R^1$ is as defined in tables 22 to 42 and $R^3$ is 8-methoxy
Tables 1051 to 1092
Compounds of the formula I.13 in which the combination of $R^1$ and $R^{61}$ is as defined in tables 1 to 21 or in which $R^1$ is as defined in tables 22 to 42 and $R^3$ is 5-trifluoromethoxy
Tables 1093 to 1134
Compounds of the formula I.13 in which the combination of $R^1$ and $R^{61}$ is as defined in tables 1 to 21 or in which $R^1$ is as defined in tables 22 to 42 and $R^3$ is 6-trifluoromethoxy
Tables 1135 to 1176
Compounds of the formula I.13 in which the combination of $R^1$ and $R^{61}$ is as defined in tables 1 to 21 or in which $R^1$ is as defined in tables 22 to 42 and $R^3$ is 7-trifluoromethoxy
Tables 1177 to 1218
Compounds of the formula I.13 in which the combination of $R^1$ and $R^{61}$ is as defined in tables 1 to 21 or in which $R^1$ is as defined in tables 22 to 42 and $R^3$ is 8-trifluoromethoxy
Tables 1219 to 2436
Compounds of the formula I.14 in which the combination of $R^1$, $R^{61}$ and $R^3$ is as defined in tables 1 to 1218
Tables 2437 to 3654
Compounds of the formula I.15 in which the combination of $R^1$, $R^{61}$ and $R^3$ is as defined in tables 1 to 1218
Tables 3655 to 4872
Compounds of the formula I.16 in which the combination of $R^1$, $R^{61}$ and $R^3$ is as defined in tables 1 to 1218
Tables 4873 to 6090
Compounds of the formula I.17 in which the combination of $R^1$, $R^{61}$ and $R^3$ is as defined in tables 1 to 1218
Tables 6091 to 6132
Compounds of the formula I.18 in which the combination of $R^1$, $R^{61}$ and $R^3$ is as defined in tables 1 to 1218

Tables 6133 to 7350
Compounds of the formula I.19 in which the combination of $R^1$, $R^{61}$ and $R^3$ is as defined in tables 1 to 1218
Tables 7351 to 8568
Compounds of the formula I.20 in which the combination of $R^1$ and $R^{61}$ is as defined in tables 1 to 21 or in which $R^1$ is as defined in tables 22 to 42 and $R^3$ is H
Tables 8569 to 8610
Compounds of the formula I.20 in which the combination of $R^1$ and $R^{61}$ is as defined in tables 1 to 21 or in which $R^1$ is as defined in tables 22 to 42 and $R^3$ is 6-methyl
Tables 8611 to 8652
Compounds of the formula I.20 in which the combination of $R^1$ and $R^{61}$ is as defined in tables 1 to 21 or in which $R^1$ is as defined in tables 22 to 42 and $R^3$ is 7-methyl
Tables 8653 to 8694
Compounds of the formula I.20 in which the combination of $R^1$ and $R^{61}$ is as defined in tables 1 to 21 or in which $R^1$ is as defined in tables 22 to 42 and $R^3$ is 8-methyl
Tables 8695 to 8736
Compounds of the formula I.20 in which the combination of $R^1$ and $R^{61}$ is as defined in tables 1 to 21 or in which $R^1$ is as defined in tables 22 to 42 and $R^3$ is 6-trifluoromethyl
Tables 8737 to 8778
Compounds of the formula I.20 in which the combination of $R^1$ and $R^{61}$ is as defined in tables 1 to 21 or in which $R^1$ is as defined in tables 22 to 42 and $R^3$ is 7-trifluoromethyl
Tables 8779 to 8820
Compounds of the formula I.20 in which the combination of $R^1$ and $R^{61}$ is as defined in tables 1 to 21 or in which $R^1$ is as defined in tables 22 to 42 and $R^3$ is 8-trifluoromethyl
Tables 8821 to 8862
Compounds of the formula I.20 in which the combination of $R^1$ and $R^{61}$ is as defined in tables 1 to 21 or in which $R^1$ is as defined in tables 22 to 42 and $R^3$ is 6-methoxy
Tables 8863 to 8904
Compounds of the formula I.20 in which the combination of $R^1$ and $R^{61}$ is as defined in tables 1 to 21 or in which $R^1$ is as defined in tables 22 to 42 and $R^3$ is 7-methoxy
Tables 8905 to 8946
Compounds of the formula I.20 in which the combination of $R^1$ and $R^{61}$ is as defined in tables 1 to 21 or in which $R^1$ is as defined in tables 22 to 42 and $R^3$ is 8-methoxy
Tables 8947 to 8988
Compounds of the formula I.20 in which the combination of $R^1$ and $R^{61}$ is as defined in tables 1 to 21 or in which $R^1$ is as defined in tables 22 to 42 and $R^3$ is 6-trifluoromethoxy
Tables 8989 to 9030
Compounds of the formula I.20 in which the combination of $R^1$ and $R^{61}$ is as defined in tables 1 to 21 or in which $R^1$ is as defined in tables 22 to 42 and $R^3$ is 7-trifluoromethoxy
Tables 9031 to 9072
Compounds of the formula I.20 in which the combination of $R^1$ and $R^{61}$ is as defined in tables 1 to 21 or in which $R^1$ is as defined in tables 22 to 42 and $R^3$ is 8-trifluoromethoxy
Tables 9073 to 10794
Compounds of the formula I.21 in which the combination of $R^1$, $R^{61}$ and $R^3$ is as defined in tables 7351 to 9072
Tables 10795 to 12516
Compounds of the formula I.22 in which the combination of $R^1$, $R^{61}$ and $R^3$ is as defined in tables 7351 to 9072
Tables 12517 to 12558
Compounds of the formula I.23 in which the combination of $R^1$, $R^{61}$ and $R^3$ is as defined in tables 7351 to 9072
Tables 12559 to 14280
Compounds of the formula I.24 in which the combination of $R^1$, $R^{61}$ and $R^3$ is as defined in tables 7351 to 9072

Tables 14281 to 16002
Compounds of the formula I.25 in which the combination of $R^1$, $R^{61}$ and $R^3$ is as defined in tables 7351 to 9072
Tables 16003 to 17724
Compounds of the formula I.26 in which the combination of $R^1$, $R^{61}$ and $R^3$ is as defined in tables 7351 to 9072

Among the above compounds of formulae I.1 to I.26 preference is given to compounds of formulae I.1, I.2, I.9, I.10, I.13, I.14, I.15, I.17 and I.18. More preference is given to compounds of formulae I.2, I.10, I.13, I.17 and I.18. Particular preference is given to compounds of formulae I.2, I.10, I.13 and I.17.

The compounds of the present invention can be prepared by analogy to routine techniques a skilled person is familiar with. In particular, the compounds of the formula I can be prepared according to the following schemes, wherein the variables, if not stated otherwise, are as defined above:

Scheme 1:

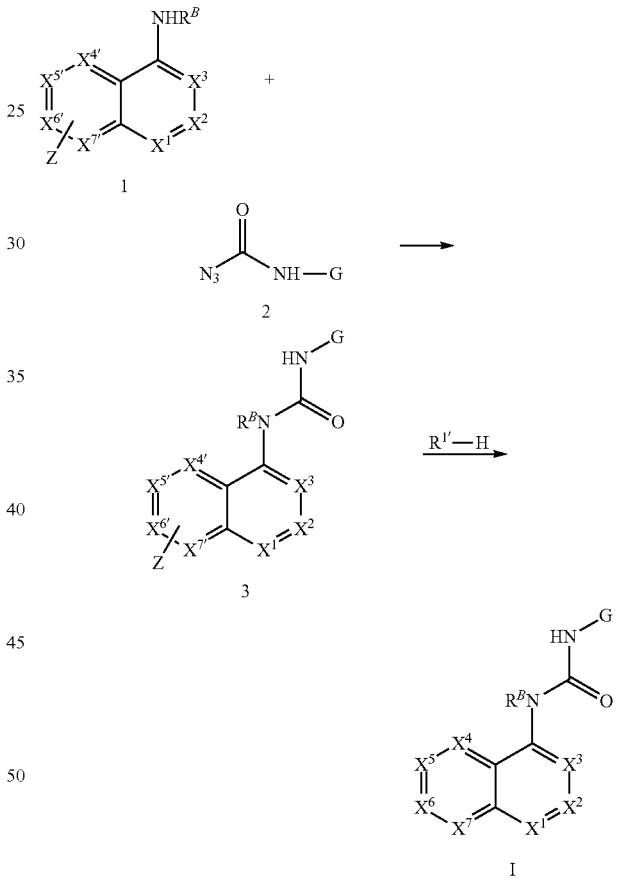

($X^{4'}$, $X^{5'}$, $X^{6'}$ and $X^{7'}$ are N or $CR^3$, where at least one of $X^{4'}$, $X^{5'}$, $X^{6'}$ and $X^{7'}$ is CH; $R^{1'}$ is a group $R^1$ bonded via a nitrogen atom to the hydrogen atom and Z is halogen)

For synthesizing compounds of formula I wherein A is $NR^B$, the amine 1 can be acylated by reaction with an acyl azide 2 (prepared by reaction of the corresponding acyl halide with a metal azide salt according to standard methods of organic chemistry) to give disubstituted ureas of general formula 3. The reaction is carried out in the presence of a suitable solvent such as toluene or N,N-dimethylformamide. The reaction is usually carried out at temperatures of from 20 to 120° C. Other conditions for describing this transformation (known as the Curtius rearrangement) are described in the following articles: Journal of Organic Chemistry, 1986, 51, 3007 & 5123; Journal of Organic Chemistry, 1987, 52, 4875; Tetrahedron Letters, 1984, 25, 3515; and Organic Reactions, 1947, 3, 337.

Substitution of Z can then be accomplished by reaction of 3 with a bi- or tricyclic amine $R^{1'}$-H to give substituted products of general formula I wherein one or two of $X^4, X^5, X^6$ and $X^7$ are $CR^1$. The substitution may be conducted with a base (e.g. NaH or $K_2CO_3$) or via a palladium-mediated coupling using a catalyst such as $Pd_2(DBA)_3$ in the presence of a ligand such as 1,1'-bis(diphenylphosphino)ferrocene. The same product may also be obtained by a 2-step procedure where a suitably mono-protected amine is reacted and then deprotected (e.g. an N—BOC derivative which is deprotected using HCl or TFA).

Disubstituted urea compounds of the general formula I, i.e. compounds of formula I wherein A is $NR^B$, can also be prepared according to the route depicted in scheme 2.

Scheme 2:

($X^{4'}, X^{5'}, X^{6'}$ and $X^{7'}$ are N or $CR^3$, where at least one of $X^{4'}$, $X^{5'}, X^{6'}$ and $X^{7'}$ is CH; $R^{1'}$ is a group $R^1$ bonded via a nitrogen atom to the hydrogen atom and Z is halogen)

The amine 1 can be acylated by reaction with an isocyanate 4 to give disubstituted ureas of general formula 3. The reaction is carried out in the presence of a suitable solvent such as toluene or N,N-dimethylformamide. The reaction is usually carried out at temperatures of from 20-120° C.

Substitution of Z can then be accomplished as described for scheme 1.

Disubstituted urea compounds of the general formula I, i.e. compounds of formula I wherein A is $NR^B$, can also be prepared according to the route depicted in scheme 3.

Scheme 3:

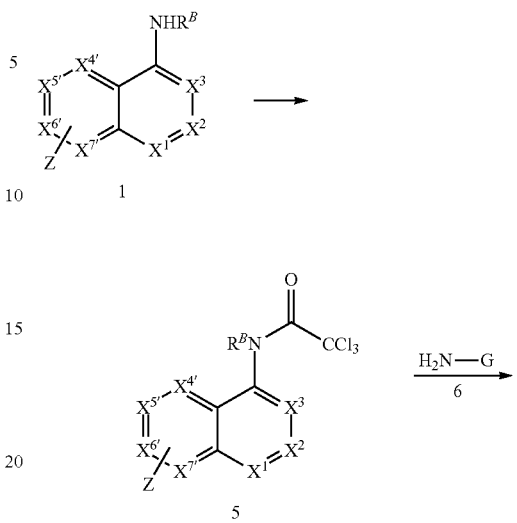

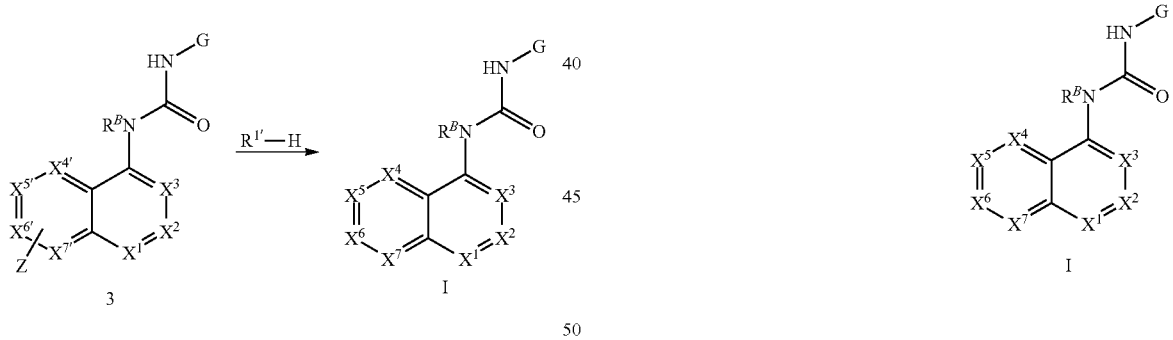

($X^{4'}, X^{5'}, X^{6'}$ and $X^{7'}$ are N or $CR^3$, where at least one of $X^{4'}$, $X^{5'}, X^{6'}$ and $X^{7'}$ is CH; $R^{1'}$ is a group $R^1$ bonded via a nitrogen atom to the hydrogen atom and Z is halogen)

The amine 1 can be converted to the trichloroacetamide 5 by reaction with trichloroacetyl chloride The reaction is carried out in the presence of a suitable solvent such as toluene or N,N-dimethylformamide. The reaction is usually carried out at temperatures of from 20-120° C. The trichloroacetamide 5 can be reacted with an amine 6 to give disubstituted ureas of general formula 3.

Substitution of Z can then be accomplished as described for scheme 1.

Amide analogs of the general formula I, i.e. compounds of formula I wherein A is $CH_2$, can be prepared according to the route depicted in scheme 4.

Scheme 4:

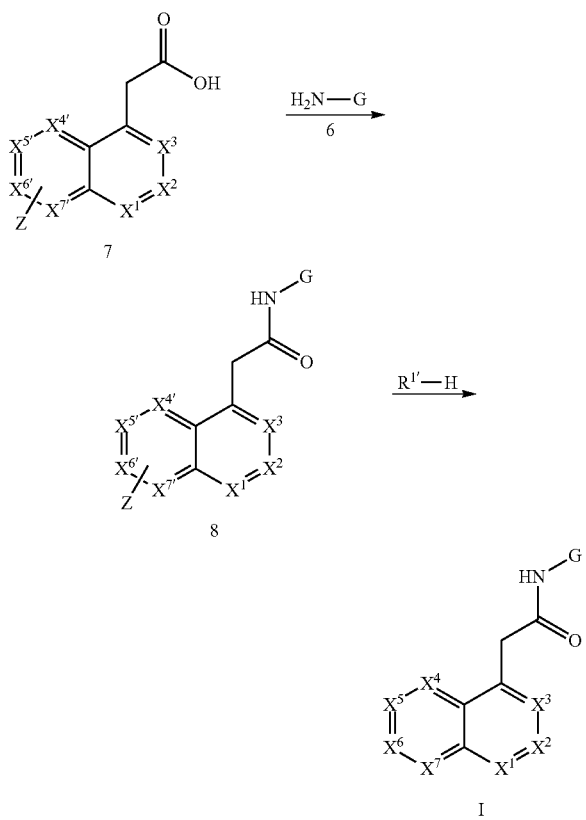

($X^{4'}$, $X^{5'}$, $X^{6'}$ and $X^{7'}$ are N or $CR^3$, where at least one of $X^{4'}$, $X^{5'}$, $X^{6'}$ and $X^{7'}$ is CH; $R^{1'}$ is a group $R^1$ bonded via a nitrogen atom to the hydrogen atom and Z is halogen)

The carboxylic acid 7 can be converted into the amide 8 by reaction with an amine 6 using standard amide formation conditions familiar to those skilled in the art. The reaction is carried out in the presence of a suitable solvent such dimethylacetamide, N,N-dimethylformamide or THF. The reaction is usually carried out at temperatures of from 20 to 120° C. Coupling reagents such as HOBT or carbonyl diimidazole are employed.

Substitution of Z can then be accomplished as described for scheme 1.

The synthesis of compounds I in which none of groups $X^4$, $X^5$, $X^6$ and $X^7$ is $CR^1$ can be accomplished by omitting the last step in the above reaction sequences or by using as starting materials amines 1 or carboxylic acids 7 which do not carry a group Z and wherein none of $X^4$, $X^5$, $X^6$ and $X^7$ is $CR^1$. Instead, the group G in compounds 2, 4 and 6 carries a radical $R^1$.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The present invention further relates to a pharmaceutical composition comprising at least one compound I, a stereoisomer, prodrug, tautomer and/or physiologically tolerated acid addition salt thereof and optionally at least one physiologically acceptable carrier and/or auxiliary substance.

The invention also relates to the use of the compound I or of a stereoisomer, prodrug, tautomer or physiologically tolerated acid addition salt thereof for the preparation of a medicament for the treatment of a disorder susceptible to the treatment with a compound that modulates, preferably inhibits, the activity of glycogen synthase kinase 3β.

Furthermore, the invention relates to a method for treating a medical disorder susceptible to treatment with a compound that modulates glycogen synthase kinase 3β activity, said method comprising administering an effective amount of at least one compound I or of a stereoisomer, prodrug, tautomer or physiologically tolerated acid addition salt thereof or of a pharmaceutical composition as defined above to a subject in need thereof.

The compounds of the formula I according to the present invention, as well as the stereoisomers, the tautomers, the prodrugs and physiologically tolerated acid addition salts thereof, are capable of modulating the activity on glycogen synthase kinase 3β. In particular, the compounds of the formula I, as well as the stereoisomers, the tautomers, the prodrugs and physiologically tolerated acid addition salts thereof, have an inhibitory activity on glycogen synthase kinase 3β. Amongst the compounds of the formula I those are preferred which achieve effective inhibition at low concentrations. In particular, compounds of the formula I are preferred which inhibit glycogen synthase kinase 3β at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

Therefore the compounds of the formula I according to the present invention, their stereoisomers, tautomers, their prodrugs and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formula I, a stereoisomer, tautomer, prodrug and/or a physiologically tolerated acid addition salt thereof, include in particular neurodegenerative diseases such as Alzheimer's disease. In addition, the compounds of the present invention are also useful for treatment of other neurodegenerative diseases such as Parkinson's disease, tauopathies (e.g. frontotemporoparietal dementia, corticobasal degeneration, Pick's disease, progressive supranuclear palsy, argyrophilic grain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma. In addition, the compounds of the present invention are also useful for treatment of schizophrenia.

Diseases which can be treated by supplying the compound of the formula I, a stereoisomer, tautomer, prodrug and/or a physiologically tolerated acid addition salt thereof, include furthermore inflammatory diseases, such as rheumatoid arthritis and osteoarthritis.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formula I involves a method. In this method, an effective quantity of one or more compounds I, a stereoisomer, tautomer, prodrug or physiologically tolerable acid addition salt thereof, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to pharmaceutical compositions for treating an individual, preferably a mammal, in particular a human being, productive animal or domestic animal. Thus, the compounds according to the invention are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the pharmaceutical compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

EXAMPLES

The compounds were either characterized via proton-NMR in $d_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation Examples

Example 1

(3aR,6aS)-Tert-butyl 5-(4-(3-pyrazin-2-ylureido) quinolin-7-yl)-hexahydropyrrolo[3,4-c]pyrrole-2 (1H)-carboxylate A solution of sodium tert-butoxide (98 mg, 1.017 mmol) and (3aR,6aS)-tert-butyl hexahydropyrrolo[3,4-c]pyrrole-2 (1H)-carboxylate (95 mg, 0.436 mmol) in THF (3 mL) was stirred under nitrogen. To this was added 1,1'-bis(diphenylphosphino)ferrocene (25 mg, 0.05 mmol), $Pd_2(DBA)_3$ (12 mg, 0.02 mmol) and 1-(7-bromoquinolin-4-yl)-3-(pyrazin-2-yl)urea (100 mg, 0.291 mmol). The mixture was then heated at reflux for 12 h before partitioning between $CH_2Cl_2$ and water. The mixture was filtered through Celite and the organic phase was separated. The water phase was extracted twice with $CH_2Cl_2$ and the combined extracts dried ($Na_2SO_4$), filtered and concentrated in vacuo to provide the crude material, which was purified by flash chromatography to give the title compound (127 mg, 83%) as a white solid.

$^1$H-NMR (DMSO, 400 MHz) δ 1.40 (s, 9H), 3.05 (s, 2H), 3.23 (s, 2H), 3.32 (m, 2H), 3.65 (m, 4H), 6.86 (s, 1H), 7.20 (d, 1H), 7.92 (d, 1H), 8.00 (d, 1H), 8.33 (s, 1H), 8.43 (s, 1H), 8.56 (d, 1H), 9.09 (s, 1H), 10.20 (m, 2H).
MS (APCI+) m/z 476.3 (M+H$^+$, 100%).

Example 2

1-(7-((3aR,6aS)-Hexahydropyrrolo[3,4-c]pyrrol-2(1H)-yl)quinolin-4-yl)-3-(pyrazin-2-yl)urea A solution of (3aR,6aS)-tert-butyl 5-(4-(3-pyrazin-2-yl)ureido)quinolin-7-yl)-hexahydro pyrrolo[3,4-c]pyrrole-2(1H)-carboxylate (54 mg, 0.11 mmol) in hydrochloric acid (4M in dioxane, 0.5 ml) was stirred at 0° C. and allowed to reach temperature over 1 h with further stirring continued for 16 h. After concentration, the product was washed with EtOAc and dried in vacuo to give the title compound (50 mg, 100%) as a yellow solid. The product was characterised as the HCl salt.
MS (APCI+) m/z 376.2 (M+H$^+$, 100%).

Example 3

(3aR,6aS)-tert-butyl 5-(6-(3-(7-methoxyquinolin-4-yl)ureido)pyrazin-2-yl)-hexahydropyrrolo[3,4-c]pyrrole-2(1H)-carboxylate The compound was prepared by the method described for Example 1 using 1-(6-bromopyrazin-2-yl)-3-(7-methoxyquinolin-4-yl)urea and (3aR,6aS)-tert-butyl hexahydropyrrolo[3,4-c]pyrrole-2(1H)-carboxylate as starting compounds and was obtained as a white solid (96 mg, 65%).
$^1$H-NMR (DMSO, 400 MHz) δ 1.40 (s, 9H), 3.05 (s, 2H), 3.18 (s, 2H), 3.32 (m, 2H), 3.55 (m, 2H), 3.70 (m, 2H), 3.95 (s, 3H), 7.32 (d, 1H), 7.38 (s, 1H), 7.65 (s, 1H), 8.10 (m, 2H), 8.41 (s, 1H), 8.69 (d, 1H), 9.65 (s, 1H), 9.75 (s, 1H).
MS (APCI+) m/z 506.3 (M+H$^+$, 100%).

Example 4

1-(6-((3aR,6aS)—Hexahydropyrrolo[3,4-c]pyrrol-2(1H)-yl)pyrazin-2-yl)-3-(7-methoxyquinolin-4-yl)urea The compound was prepared by the method described for Example 2 using (3aR,6aS)-tert-butyl 5-(6-(3-(7-methoxyquinolin-4-yl)ureido)pyrazin-2-yl)hexahydro-pyrrolo[3,4-c]pyrrole-2(1H)-carboxylate as starting compound and was obtained as a yellow solid (72 mg, 100%). The product was characterised as the HCl salt.
$^1$H-NMR (DMSO, 400 MHz) δ 3.15 (m, 4H), 3.18 (s, 2H), 3.5-3.7 (m, 6H), 4.02 (s, 3H), 7.50 (s, 1H), 7.61 (d, 1H), 7.77 (s, 1H), 8.53 (s, 1H), 8.61 (d, 1H), 8.78 (d, 1H), 8.92 (m, 2H), 10.40 (s, 1H), 10.96 (s, 1H).
MS (APCI+) m/z 406.2 (M+H$^+$, 30%).

Example 5

(1S,4S)-Tert-butyl 5-(4-(3-pyrazin-2-ylureido)quinolin-7-yl)-2,5-diaza bicyclo[2.2.1]-heptane-2-carboxylate The compound was prepared by the method described for Example 1 using 1-(7-bromoquinolin-4-yl)-3-(pyrazin-2-yl)urea and (1S,4S)-tert-butyl 2,5-diazabicyclo[2.2.1]-heptane-2-carboxylate as starting compounds.
MS (APCI+) m/z 462.3 (M+H$^+$, 100%).

Example 6

Tert-butyl 5-(4-(3-pyrazin-2-ylureido)quinolin-7-yl) hexahydropyrrolo[3,4-b]pyrrole-1(2H)-carboxylate The compound was prepared by the method described for Example 1 using 1-(7-bromoquinolin-4-yl)-3-(pyrazin-2-yl)urea and tert-butyl hexahydropyrrolo[2,3-c]pyrrole-1(2H)-carboxylate as starting compounds.
MS (APCI+) m/z 476.1 (M+H$^+$), 419.1 (M-tBu+H$^+$, 100%).

Example 7

1-(7-((1S,4S)-2,5-Diazabicyclo[2.2.1]heptan-2-yl)quinolin-4-yl)-3-(pyrazin-2-yl)urea The compound was prepared by the method described for Example 2 using (1S,4S)tert-butyl 5-[4-(3-pyrazin-2-yl-ureido)-quinolin-7-yl]-2,5-diazabicyclo[2.2.1]heptane-2-carboxylate from example 5 as starting compound.
MS (APCI+) m/z 362.2 (M+H$^+$).

Example 8

1-(6-(Dihydro-1H-furo[3,4-c]pyrrol-5(3H,6H,6aH)-yl)quinolin-4-yl)-3-(pyrazin-2-yl)urea The compound was prepared by the method described for Example 1 using hexahydro-furo[3,4-c]pyrrole and 1-(6-bromoquinolin-4-yl)-3-(pyrazin-2-yl)urea as starting compounds.
MS (APCI+) m/z 377.2 (M+H$^+$).

Example 9

1-(6-(Dihydro-1H-furo[3,4-c]pyrrol-5(3H,6H,6aH)-yl)pyridin-2-yl)-3-(7-methoxyquinolin-4-yl)urea The compound was prepared by the method described for Example 1.
MS (APCI+) m/z 406.1 (M+H$^+$).

Example 10

1-(6-((1S,4S)-2-Oxa-5-azabicyclo[2.2.1]heptan-5-yl)pyridin-2-yl)-3-(7-methoxyquinolin-4-yl)urea The compound was prepared by the method described for Example 1.
MS (APCI+) m/z 392.2 (M+H$^+$).

Example 11

(1S,4S)-Tert-butyl 5-(4-(3-pyrazin-2-ylureido)quinolin-6-yl)-2,5-diazabicyclo[2.2.1]heptane-2-carboxylate The compound was prepared by the method described for Example 1.
MS (APCI+) m/z 462.2 (M+H$^+$).

Example 12

1-(7-(Hexahydropyrrolo[3,4-b]pyrrol-5(1H)-yl)quinolin-4-yl)-3-(pyrazin-2-yl)urea The compound was prepared by the method described for Example 2 starting from tert-butyl 5-(4-(3-pyrazin-2-ylureido)quinolin-7-yl)hexahydropyrrolo[3,4-b]pyrrole-1(2H)-carboxylate from example 6.
MS (APCI+) m/z 376.2 (M+H$^+$).

II. Biological Tests

The compounds according to the invention exhibit very good affinities for GSK-3 (<1 µM, frequently <100 nM) and exhibited good selectivity against multiple kinase targets.

Methods—Biochemical hGSK-3Beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 µCi 33P-ATP, 10 µM ATP, 0.0125U hGSK-3β (Upstate cell signaling solutions) and 1 µM substrate (biotin-YRRAAVPPSPSLSRHSSPHQ (pS)EDEEE) in 50 mM HEPES, 10 mM $MgCl_2$, 100 mM $Na_3VO_4$, 1 mM DTT, 0.0075% Triton, 2% DMSO (total volume 50 µL) for 30 minutes at room temperature. The incubation was stopped by addition of an equal volume of 100 mM EDTA, 4M NaCl. 80 µL of this mixture was added to streptavidin-coated Flashplates (PerkinElmer). Following a wash step, 33P incorporation was quantified on a MicroBeta microplate liquid scintillation counter (PerkinElmer). $IC_{50}$s were determined by fitting a sigmoidal dose-response curve to the counts obtained at the different concentrations in GraphPad Prism.

Methods—β-Catenin Reporter-Gene Assay

Compounds were tested for their ability to modulate β-catenin-modulated gene transcription in a LEF/TCF (T-cell factor) reporter gene assay. SY-SY5Y human neuroblastoma cells were transiently transfected with 80 ng/well TOP-FLASH plasmid (Upstate cell signaling solutions) containing two sets of three copies of the TCF binding site upstream of the Thymidine Kinase minimal promoter and firefly Luciferase open reading frame or with 80 ng/well FOP-FLASH plasmid (Upstate cell signaling solutions) containing three copies of a mutated TCF binding site upstream of the Thymidine Kinase minimal promoter and firefly Luciferase open reading frame. In addition all cells were transiently transfected with the 20 ng/well pRL-TK plasmid (Promega) containing the herpes simplex virus thymidine kinase promoter to provide low to moderate levels of *Renilla* Luciferase expression. Transfection medium was exchanged for serum-free medium containing the test substance and incubated for 24 h at 37 degreedC. The incubation was stopped and quantified using the Dual Glo Luciferase Assay (Promega) as indicated and quantified on a Pherastar reader (BMG).

Firefly Luciferase activity was normalised for *Renilla* Luciferase activity per well. Subsequently, the normalised TOPFLASH response was compared to the normalised FOPFLASH response, thus giving the LEF/TCF specific signal. The maximal response is the maximal ratio between the normalised TOPFLASH and FOPFLASH signals. Sigmoidal dose-response curves were fitted using Graphpad Prism.

The results of the binding tests are given in the table below.

| Example | GSK-3β $IC_{50}$ |
| --- | --- |
| 1 | ++ |
| 3 | ++ |
| 7 | ++ |
| 8 | +++ |
| 9 | +++ |
| 10 | +++ |
| 11 | ++ |
| 12 | ++ |

GSK-3β $IC_{50}$:
+ >10 µM
++ from 100 nM to 10 µM
+++ <100 nM

We claim:
1. A heterocyclic compound of the general formula (I)

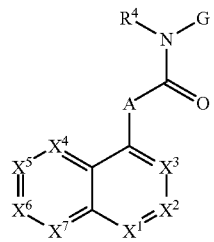

the stereoisomers, tautomers and/or physiologically tolerated acid addition salts thereof, wherein
A is selected from the group consisting of $CR^{A1}R^{A2}$ and $NR^B$; where
  $R^{A1}$ and $R^{A2}$ are independently of each other selected from the group consisting of hydrogen, $C_1$-$C_2$-alkyl, $C_1$-$C_2$-haloalkyl, $NH_2$ and OH; and
  $R^B$ is selected from H, $C_1$-$C_4$-alkyl and $C_1$-$C_4$-haloalkyl;
$X^1$ is selected from the group consisting of $CR^2$ and N;
$X^2$ and $X^3$ are independently of each other selected from the group consisting of $CR^2$;
$X^4$ and $X^7$ are independently of each other selected from the group consisting of $CR^1$, $CR^3$ and N;
$X^5$ and $X^6$ are independently of each other selected from the group consisting of $CR^1$ and $CR^3$;
With the proviso that only one of $X^1$, $X^4$ and $X^7$ is N and that no more than two of $X^4$, $X^5$, $X^6$ and $X^7$ are $CR^1$;
G is a 5- or 6-membered heteroaromatic ring containing one nitrogen atom and optionally 1, 2 or 3 further nitrogen atoms as ring members, where the heteroaromatic ring is bonded to the group $NR^4$ via a carbon atom in α-position to the nitrogen ring atom and where the heteroaromatic ring optionally carries 1, 2, 3 or 4 substituents $R^5$ or 1, 2 or 3 substituents $R^5$ and 1 substituent $R^1$; with the proviso that G carries one substituent $R^1$ if none of $X^4$, $X^5$, $X^6$ and $X^7$ is $CR^1$;
each $R^1$ is independently a 6-, 7-, 8-, 9-, 10-, 11-, 12-, 13- or 14-membered bicyclic or tricyclic saturated or unsaturated heterocyclic ring containing one nitrogen atom and optionally 1, 2 or 3 further heteroatoms selected from N, O and S as ring members and optionally carrying 1, 2 or 3 substituents $R^6$;
each $R^2$ is independently selected from the group consisting of hydrogen, OH, halogen, CN, $C_1$-$C_6$-alkyl, $C_1$-$C_6$-haloalkyl, $C_1$-$C_6$-alkoxy, $C_1$-$C_6$-haloalkoxy and $NR^aR^b$; or two radicals $R^2$ bonded at the carbon atoms of groups $X^2$ and $X^3$, together with the carbon atoms to which they are bonded, form a 5- or 6-membered saturated or unsaturated ring which may contain 1 or 2 heteroatoms as ring members selected from the group consisting of N, O and S and which optionally carries 1, 2 or 3 substituents $R^7$;
each $R^3$ is independently selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^8$ and wherein Ar may also be bonded via a $CH_2$ group;

$R^4$ is selected from the group consisting of hydrogen, $C_1$-$C_4$-alkyl and $C_1$-$C_4$-haloalkyl;

$R^5$, $R^6$ and $R^7$, independently of each other and independently of each occurrence, have one of the meanings given for $R^3$;

each $R^8$ is independently selected from the group consisting of halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, a phenyl group and an aromatic 5- or 6-membered C-bound heteroaromatic radical comprising one nitrogen atom and optionally 1, 2 or 3 further heteroatoms independently selected from O, S and N as ring members, wherein phenyl and the heteroaromatic radical are, independently of each other, unsubstituted or substituted by 1, 2, 3 or 4 radicals selected from halogen, cyano, $C_1$-$C_4$-alkyl, $C_1$-$C_4$-haloalkyl, $C_1$-$C_4$-alkoxy and $C_1$-$C_4$-haloalkoxy; and $R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-haloalkylcarbonyl;

or $R^a$ and $R^b$ form, together with the nitrogen atom to which they are bonded, a 3-, 4-, 5-, 6- or 7-membered saturated or unsaturated aromatic or non-aromatic N-heterocyclic ring, which may contain 1 further heteroatom or heteroatom containing group selected from the group consisting of O, S, SO, $SO_2$ and N as a ring member.

2. The heterocyclic compound according to claim 1, wherein one or two of $X^4$, $X^5$, $X^6$ and $X^7$ are $CR^1$.

3. The heterocyclic compound according to claim 1, wherein none of $X^4$, $X^5$, $X^6$ and $X^7$ is $CR^1$ and G carries a substituent R1.

4. The heterocyclic compound according to claim 1, wherein $X^1$ is N.

5. The heterocyclic compound according to claim 4, wherein $X^4$ is $CR^1$ or $CR^3$.

6. The heterocyclic compound according to claim 1, wherein $R^1$ is a 7-, 8-, 9- or 10-membered bicyclic saturated heterocyclic ring containing one nitrogen atom and optionally 1, 2 or 3 further heteroatoms selected from N and O as ring members and optionally carrying 1, 2 or 3 substituents $R^6$ which are as defined in claim 1.

7. The heterocyclic compound according to claim 6, wherein $R^1$ is a 7-, 8-, 9- or 10- membered bicyclic saturated heterocyclic ring bound via a nitrogen ring atom, optionally containing one further heteroatom selected from N and O as ring member and optionally carrying 1, 2 or 3 substituents $R^6$.

8. The heterocyclic compound according to claim 1, wherein $R^6$ is selected from $C_1$-$C_4$-alkyl, $C_1$-$C_4$fluoroalkyl, $C_1$-$C_4$-alkoxy, $C_1$-$C_4$-fluoroalkoxy, $C_1$-$C_4$-alkylcarbonyl, $C_1$-$C_4$-fluoroalkylcarbonyl, $C_1$-$C_4$-alkoxycarbonyl and $C_1$-$C_4$-fluoroalkoxycarbonyl.

9. The heterocyclic compound according to claim 1, wherein $R^1$ is selected from one of the following formulae

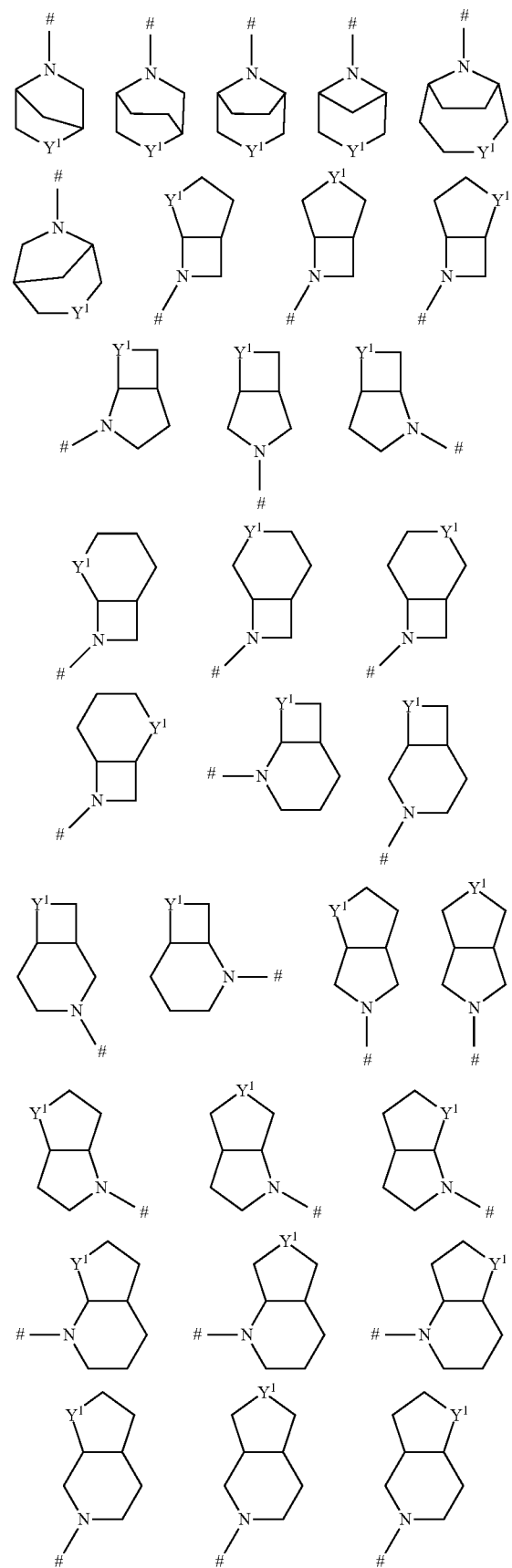

-continued

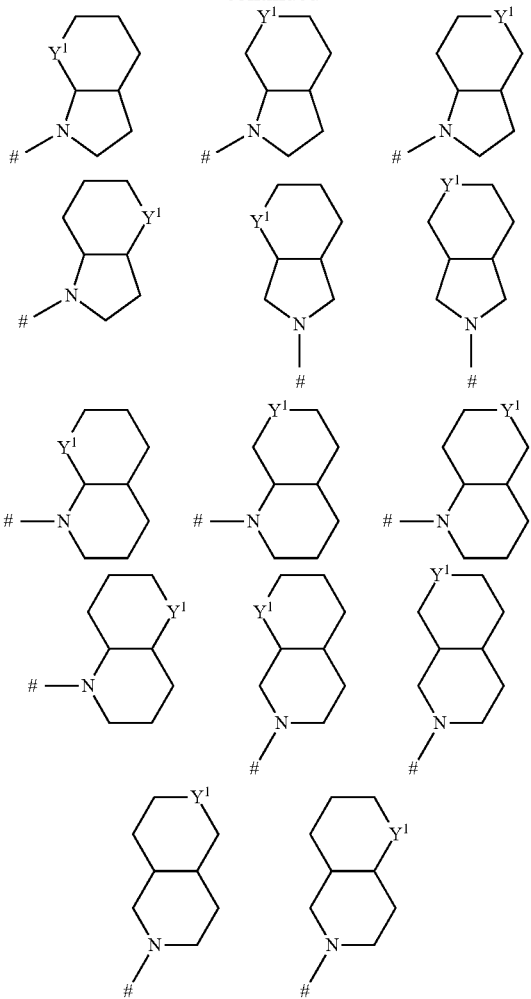

and the stereoisomers thereof;
where
$Y^1$ is O or $NR^{61}$;
$R^{61}$ is H or has one of the meanings of $R^6$ given in claim 1; and
# is the attachment point to the remainder of the molecule.

10. The heterocyclic compound according to claim 1, wherein each $R^3$ is independently selected from hydrogen, halogen, $C_1$-$C_4$-alkyl, $C_1$-$C_4$-fluoroalkyl, $C_1$-$C_4$-alkoxy and $C_1$-$C_4$-fluoroalkoxy.

11. The heterocyclic compound according to claim 1, wherein each $R^2$ is independently selected from hydrogen, halogen, $C_1$-$C_4$-alkyl and $C_1$-$C_4$-fluoroalkyl.

12. The heterocyclic compound according to claim 1, wherein one of groups $X^1$, $X^2$ and $X^3$ is CH and one of groups $X^1$, $X^2$ and $X^3$ is $CR^2$, where $R^2$ has one of the meanings given in claim 1.

13. The heterocyclic compound according to claim 1, wherein $X^1$ is N, $X^2$ and $X^3$ are $CR^2$, preferably CH, one of $X^5$ and $X^6$ is $CR^1$ and the other is $CR^3$, preferably CH, $X^4$ and $X^7$ are $CR^3$, preferably CH, and G carries no substituent $R^1$; or $X^1$ is N, $X^2$ and $X^3$ are $CR^2$, preferably CH, $X^4$, $X^5$ and $X^7$ are $CR^3$, preferably CH, $X^6$ is $CR^3$, preferably C-methoxy, and G carries one substituent $R^1$.

14. The heterocyclic compound according to claim 1, wherein G is a 6-membered heteroaromatic ring selected from pyridin-2-yl, pyrazin-2-yl, pyrimidin-2-yl, pyrimidin-4-yl, pyridazin-3-yl and triazin-2-yl, which may carry 1, 2, or 3 substituents $R^5$ which are as defined in claim 1 or which may carry 1 or 2 substituents $R^5$ which are as defined in claim 1 and one substituent $R^1$ which is defined in claim 1.

15. The heterocyclic compound according to claim 14, wherein G is a 6-membered heteroaromatic ring selected from pyridin-2-yl and pyrazin-2-yl, which may carry 1, 2, or 3 substituents $R^5$ which are as defined in claim 1 or which may carry 1 or 2 substituents $R^5$ which are as defined in claim 1 and one substituent $R^1$ which is as defined in claim 1.

16. The heterocyclic compound according to claim 15, wherein G carries the substituent $R^1$ in the 6-position.

17. The heterocyclic compound according to claim 1, wherein A is $CH_2$, NH or $NCH_3$.

18. The heterocyclic compound according to claim 1, wherein $R^4$ is H or $CH_3$.

19. A pharmaceutical composition comprising at least one heterocyclic compound as defined in claim 1, a stereoisomer, tautomer and/or physiologically tolerated acid addition salt thereof and optionally at least one physiologically acceptable carrier and/or auxiliary substance.

* * * * *

UNITED STATES PATENT AND TRADEMARK OFFICE
CERTIFICATE OF CORRECTION

| | | |
|---|---|---|
| PATENT NO. | : 8,455,648 B2 | Page 1 of 1 |
| APPLICATION NO. | : 12/988833 | |
| DATED | : June 4, 2013 | |
| INVENTOR(S) | : Turner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this
Sixth Day of January, 2015

Michelle K. Lee
*Deputy Director of the United States Patent and Trademark Office*